United States Patent
Hoey

(10) Patent No.: US 8,579,893 B2
(45) Date of Patent: Nov. 12, 2013

(54) MEDICAL SYSTEM AND METHOD OF USE

(75) Inventor: Michael Hoey, Shoreview, MN (US)

(73) Assignee: Tsunami MedTech, LLC, Menlo Park, CA (US)

( * ) Notice: Subject to any disclaimer, the term of this patent is extended or adjusted under 35 U.S.C. 154(b) by 148 days.

(21) Appl. No.: 12/692,488

(22) Filed: Jan. 22, 2010

(65) Prior Publication Data

US 2010/0185189 A1  Jul. 22, 2010

Related U.S. Application Data

(63) Continuation of application No. 11/462,324, filed on Aug. 3, 2006, now abandoned.

(60) Provisional application No. 60/705,081, filed on Aug. 3, 2005, provisional application No. 60/720,975, filed on Sep. 27, 2005, provisional application No. 60/780,924, filed on Mar. 9, 2006, provisional application No. 60/814,937, filed on Jun. 19, 2006.

(51) Int. Cl.
 *A61B 18/18* (2006.01)
(52) U.S. Cl.
 USPC .............................................. 606/41; 606/28
(58) Field of Classification Search
 USPC .................. 239/556–559, 267; 600/153–158; 606/27–28
 See application file for complete search history.

(56) References Cited

U.S. PATENT DOCUMENTS

| | | |
|---|---|---|
| 408,899 A | 8/1889 | Bioch et al. |
| 697,181 A | 4/1902 | Smith |
| 1,719,750 A | 9/1927 | Bridge et al. |
| 3,818,913 A | 6/1974 | Wallach |
| 3,880,168 A | 4/1975 | Berman |
| 3,930,505 A | 1/1976 | Wallach |
| 4,024,866 A | 5/1977 | Wallach |
| 4,083,077 A | 4/1978 | Knight et al. |
| 4,672,962 A | 6/1987 | Hershenson |
| 4,682,596 A | 7/1987 | Bales et al. |
| 4,748,979 A | 6/1988 | Hershenson |

(Continued)

FOREIGN PATENT DOCUMENTS

| | | |
|---|---|---|
| WO | WO 00/11927 | 3/2000 |
| WO | WO 00/29055 | 5/2000 |

(Continued)

OTHER PUBLICATIONS

Coda, et al., "Effects of pulmonary reventilation on gas exchange after cryolytic disobstruction of endobronchial tumors," *Minerva Medical*, vol. 72, pp. 1627-1631, Jun. 1981 (with English translation).

(Continued)

*Primary Examiner* — Linda Dvorak
*Assistant Examiner* — Jaymi Della
(74) *Attorney, Agent, or Firm* — Levine Bagade Han LLP

(57) ABSTRACT

A tissue evacuation device may be designed to provide a high-energy fluid (e.g., a heated vapor) to targeted tissue for breaking down the targeted tissue, such as the nucleus of an intervertebral disc. An inner tube positioned within an outer tube, having a nozzle coupled to distal ends of the tubes, having a heating element positioned between the inner and outer tubes, delivers a heated vapor through a port to the nozzle to break down tissue. After the nucleus or other targeted tissue is broken down, the tissue evacuation device may also remove some or all of the broken down tissue.

18 Claims, 12 Drawing Sheets

(56) References Cited

U.S. PATENT DOCUMENTS

| | | |
|---|---|---|
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,950,266 A | 8/1990 | Sinofsky |
| 4,985,027 A | 1/1991 | Dressel |
| 5,006,119 A | 4/1991 | Acker et al. |
| 5,011,566 A | 4/1991 | Hoffman |
| 5,084,043 A | 1/1992 | Hertzmann et al. |
| 5,102,410 A | 4/1992 | Dressel |
| 5,112,328 A | 5/1992 | Taboada et al. |
| 5,122,138 A | 6/1992 | Manwaring |
| 5,158,536 A | 10/1992 | Sekins et al. |
| 5,190,539 A | 3/1993 | Fletcher et al. |
| 5,217,459 A | 6/1993 | Kamerling |
| 5,217,465 A | 6/1993 | Steppe |
| 5,263,951 A | 11/1993 | Spears et al. |
| 5,277,696 A | 1/1994 | Hagen |
| 5,298,298 A | 3/1994 | Hoffman |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,542,928 A | 8/1996 | Evans et al. |
| 5,549,628 A | 8/1996 | Cooper et al. |
| 5,554,172 A | 9/1996 | Horner et al. |
| 5,562,608 A | 10/1996 | Sekins et al. |
| 5,575,803 A | 11/1996 | Cooper et al. |
| 5,584,872 A | 12/1996 | LaFontaine et al. |
| 5,591,157 A | 1/1997 | Hennings et al. |
| 5,591,162 A | 1/1997 | Fletcher et al. |
| 5,616,120 A | 4/1997 | Andrew et al. |
| 5,620,440 A | 4/1997 | Heckele et al. |
| 5,669,907 A | 9/1997 | Platt, Jr. et al. |
| 5,681,282 A | 10/1997 | Eggers et al. |
| 5,683,366 A | 11/1997 | Eggers et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,735,811 A | 4/1998 | Brisken |
| 5,741,247 A | 4/1998 | Rizoiu et al. |
| 5,741,248 A | 4/1998 | Stern et al. |
| 5,752,965 A | 5/1998 | Francis et al. |
| 5,755,753 A | 5/1998 | Knowlton |
| 5,782,914 A | 7/1998 | Schankereli |
| 5,785,521 A | 7/1998 | Rizoiu et al. |
| 5,800,482 A | 9/1998 | Pomeranz et al. |
| 5,810,764 A | 9/1998 | Eggers et al. |
| 5,824,703 A | 10/1998 | Clark, Jr. |
| 5,827,268 A | 10/1998 | Laufer |
| 5,843,019 A | 12/1998 | Eggers et al. |
| 5,843,073 A | 12/1998 | Sinofsky |
| 5,871,469 A | 2/1999 | Eggers |
| 5,879,329 A | 3/1999 | Ginsburg |
| 5,885,243 A | 3/1999 | Capetan et al. |
| 5,888,198 A | 3/1999 | Eggers et al. |
| 5,891,095 A | 4/1999 | Eggers et al. |
| 5,891,134 A | 4/1999 | Goble et al. |
| 5,913,856 A | 6/1999 | Chia et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu |
| 5,980,504 A | 11/1999 | Sharkey et al. |
| 5,986,662 A | 11/1999 | Argiro et al. |
| 5,989,212 A | 11/1999 | Sussman et al. |
| 5,989,238 A | 11/1999 | Ginsburg |
| 5,989,249 A | 11/1999 | Kirwin |
| 5,989,445 A | 11/1999 | Wise et al. |
| 5,997,499 A | 12/1999 | Sussman et al. |
| 6,024,733 A | 2/2000 | Eggers et al. |
| 6,027,501 A | 2/2000 | Goble et al. |
| 6,032,077 A | 2/2000 | Pomeranz |
| 6,032,674 A | 3/2000 | Eggers et al. |
| 6,047,700 A | 4/2000 | Eggers et al. |
| 6,053,909 A | 4/2000 | Shadduck |
| 6,056,746 A | 5/2000 | Goble et al. |
| 6,059,011 A | 5/2000 | Giolo |
| 6,063,079 A | 5/2000 | Hovda et al. |
| 6,063,081 A | 5/2000 | Mulier et al. |
| 6,066,134 A | 5/2000 | Eggers et al. |
| 6,074,358 A | 6/2000 | Andrew et al. |
| 6,080,128 A | 6/2000 | Sussman et al. |
| 6,080,151 A | 6/2000 | Swartz et al. |
| 6,083,255 A | 7/2000 | Laufer et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,106,516 A | 8/2000 | Bmassengill |
| 6,110,162 A | 8/2000 | Sussman et al. |
| 6,113,722 A | 9/2000 | Hoffman et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,194 A | 12/2000 | Eggers et al. |
| 6,162,232 A | 12/2000 | Shadduck |
| 6,168,594 B1 | 1/2001 | LaFontaine et al. |
| 6,174,308 B1 | 1/2001 | Goble et al. |
| 6,179,805 B1 | 1/2001 | Sussman et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |

(56) References Cited

U.S. PATENT DOCUMENTS

| | | |
|---|---|---|
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengil |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B2 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Wolosko et al. |
| 6,896,675 B2 | 5/2005 | Leung et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,972,014 B2 | 12/2005 | Eum et al. |
| 6,986,769 B2 | 1/2006 | Nelson et al. |
| 6,991,028 B2 | 1/2006 | Comeaux et al. |
| 6,991,631 B2 | 1/2006 | Wolosko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,192,400 B2 | 3/2007 | Campbell et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,549,987 B2 | 6/2009 | Shadduck |
| 7,585,295 B2 | 9/2009 | Ben-Nun |
| 7,674,259 B2 | 3/2010 | Shadduck |
| 7,892,229 B2 | 2/2011 | Shadduck et al. |
| 8,016,823 B2 | 9/2011 | Shadduck |
| 8,187,269 B2 | 5/2012 | Shadduck et al. |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0049438 A1 | 4/2002 | Sharkey et al. |
| 2002/0077516 A1 | 6/2002 | Flanigan |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0133147 A1 | 9/2002 | Marchitto et al. |
| 2002/0161326 A1 | 10/2002 | Sussman et al. |
| 2002/0177846 A1 | 11/2002 | Mulier et al. |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |

(56) References Cited

U.S. PATENT DOCUMENTS

| | | |
|---|---|---|
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068306 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0161233 A1 | 7/2006 | Barry et al. |
| 2006/0200076 A1 | 9/2006 | Gonzalez et al. |
| 2006/0224154 A1 | 10/2006 | Shadduck et al. |
| 2007/0036417 A1 | 2/2007 | Argiro et al. |
| 2007/0091087 A1 | 4/2007 | Zuiderveld |
| 2007/0265687 A1 | 11/2007 | Deem et al. |
| 2008/0033493 A1 | 2/2008 | Deckman et al. |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0132826 A1 | 6/2008 | Shadduck et al. |
| 2009/0105702 A1 | 4/2009 | Shadduck |
| 2009/0105703 A1 | 4/2009 | Shadduck |
| 2009/0149846 A1 | 6/2009 | Hoey et al. |
| 2009/0216220 A1 | 8/2009 | Hoey et al. |
| 2009/0312753 A1 | 12/2009 | Shadduck |
| 2010/0076416 A1 | 3/2010 | Hoey et al. |
| 2010/0160905 A1 | 6/2010 | Shadduck |
| 2010/0179528 A1 | 7/2010 | Shadduck et al. |
| 2010/0204688 A1 | 8/2010 | Hoey et al. |
| 2010/0262133 A1 | 10/2010 | Hoey et al. |
| 2011/0077628 A1 | 3/2011 | Hoey et al. |
| 2011/0118717 A1 | 5/2011 | Shadduck |
| 2011/0160648 A1 | 6/2011 | Hoey |
| 2011/0264090 A1 | 10/2011 | Shadduck et al. |
| 2012/0065632 A1 | 3/2012 | Shadduck |
| 2012/0259271 A1 | 10/2012 | Shadduck et al. |

FOREIGN PATENT DOCUMENTS

| | | |
|---|---|---|
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema." *N. Engl J Med.* vol. 348, No. 21, pp. 2059-2073, May 22, 2003.

Homasson, et al., "Bronchoscopic cryotherapy for airway strictures caused by tumors." *Chest.* vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723, Sep. 1996.

Morice et al. "Endobrinchial argon plasma coagulation for treatment of hemoptysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure steam," *Advancesin Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT Scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography." *Annu. Rev. Mater. Sci.*, vol. 28, pp. 153-184, 1998, accessed at http://www.bwfoundry.com/xia.pdf.

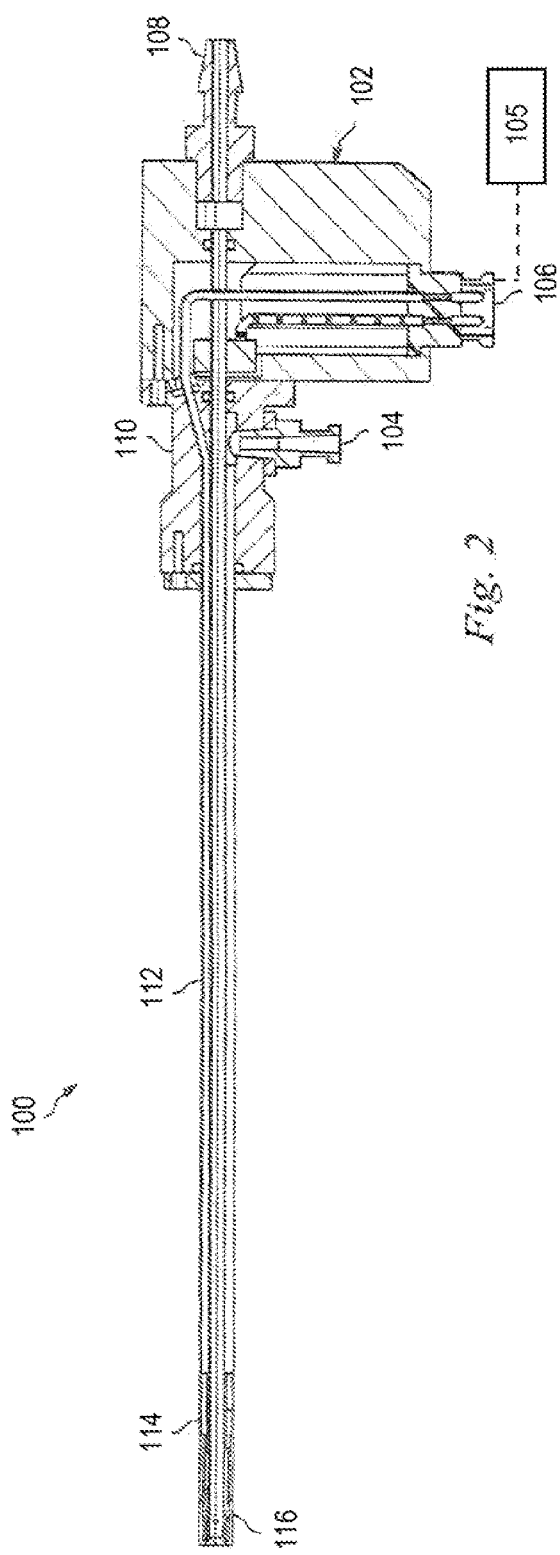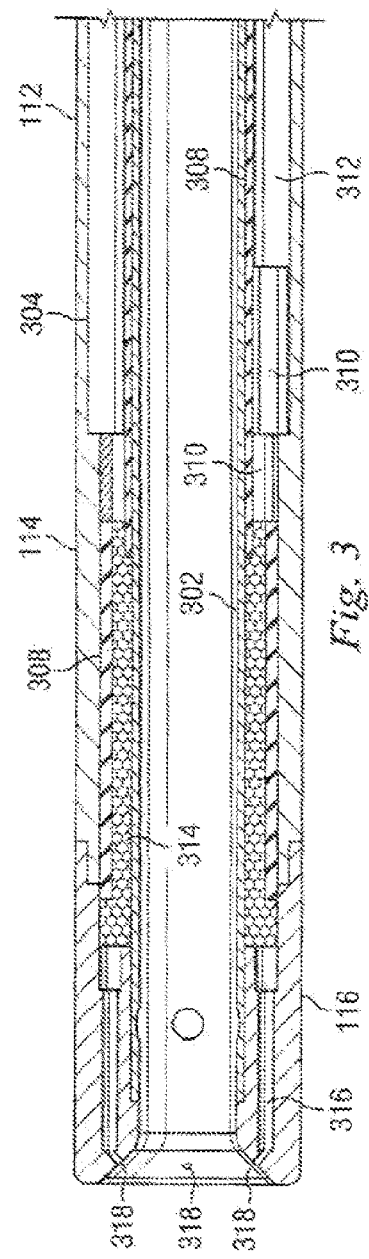

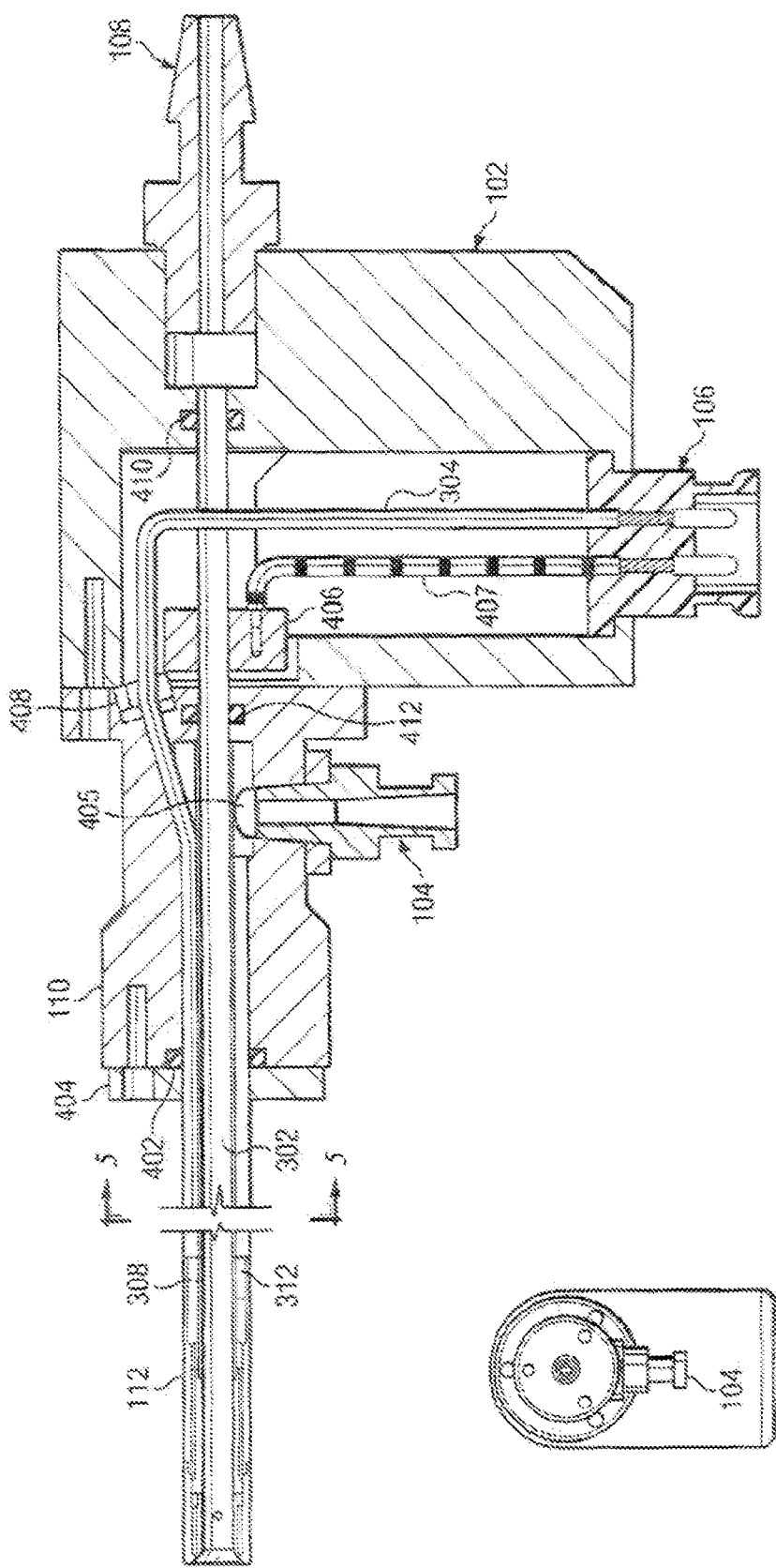

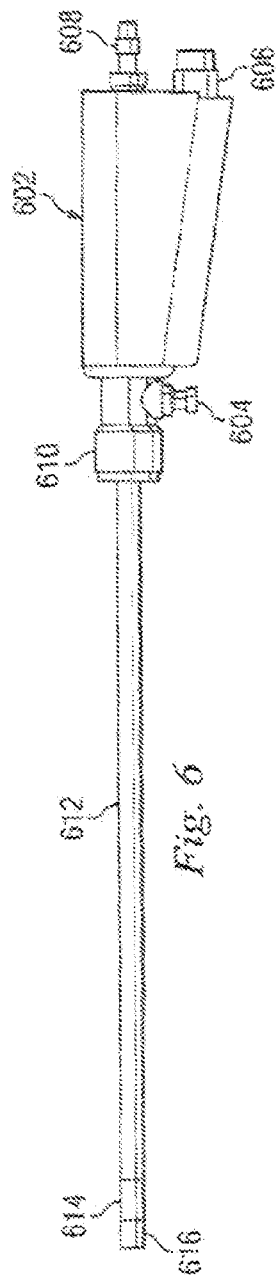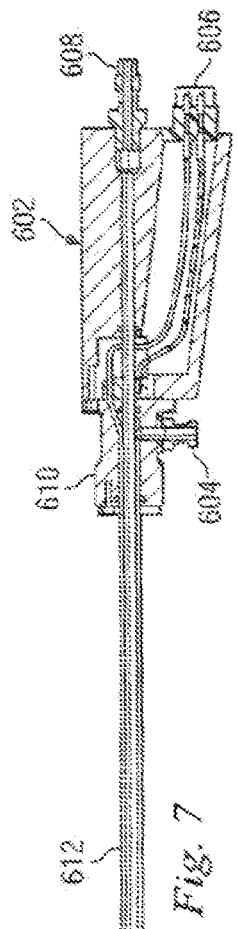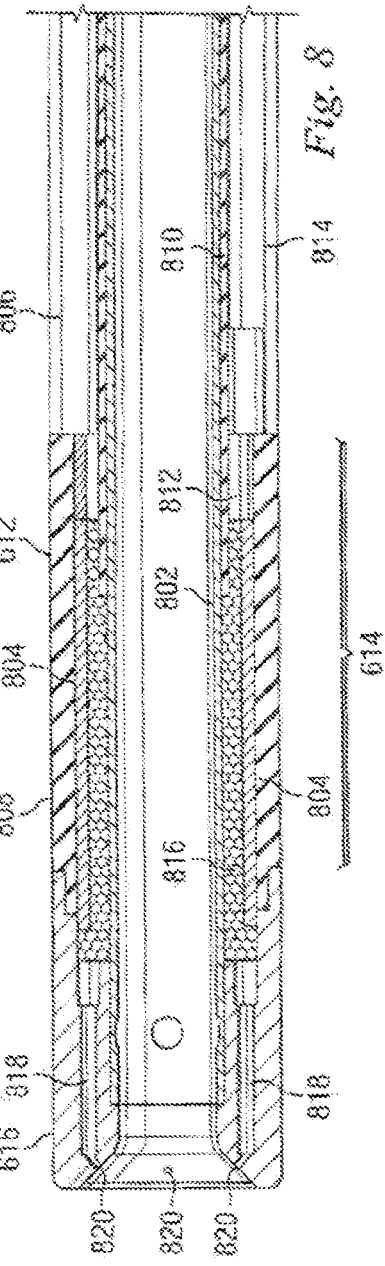

MEDICAL SYSTEM AND METHOD OF USE

CROSS-REFERENCE TO RELATED APPLICATIONS

This application is a continuation of U.S. patent application Ser. No. 11/462,324, entitled "Tissue Evacuation Device," filed Aug. 3, 2006 which claims priority to commonly assigned U.S. Provisional Application Ser. No. 60/705,081, entitled "Tissue Vaporization Instrument," filed Aug. 3, 2005; and U.S. Provisional Application Ser. No. 60/720,975, entitled "Tissue Evacuation Device," filed Sep. 27, 2005, and U.S. Provisional Application Ser. No. 60/780,924, entitled "Tissue Evacuation Device," filed Mar. 9, 2006, and U.S. Provisional Application Ser. No. 60/814,937, entitled "Tissue Evacuation Device," filed Jun. 19, 2006, all of which are hereby incorporated by reference.

FIELD OF THE INVENTION

This patent application relates to a medical instrument and, more particularly, to a surgical instrument for vaporizing tissue.

BACKGROUND

A variety of spinal surgeries, such as nucleus replacement, spinal fusion, and artificial disc replacement, include removing the nucleus of an intervertebral disc in a procedure called a nuclectomy. An intervertebral disc includes a nucleus and an annulus. The nucleus is a soft caliginous center of the disc, and the annulus is a harder caliginous outer ring of the disc. Accordingly, there is a difference in the composition of nucleus tissue and annulus tissue. During a nuclectomy, it is important that the surgeon removes the nucleus without damaging the annulus or the endplates of the adjacent vertebral bodies. However, performing a nuclectomy while minimizing or eliminating damage to surrounding tissues is a difficult task.

BRIEF SUMMARY OF THE INVENTION

A tissue evacuation device may be designed to provide a high-energy fluid (e.g., a heated vapor) to targeted tissue for breaking down the targeted tissue, such as the nucleus of an intervertebral disc. An inner tube positioned within an outer tube, having a nozzle coupled to distal ends of the tubes, having a heating element positioned between the inner and outer tubes, delivers a heated vapor through a port to the nozzle to break down tissue. After the nucleus or other targeted tissue is broken down, the tissue evacuation device may also remove some or all of the broken down tissue.

BRIEF DESCRIPTION OF THE SEVERAL VIEWS OF THE DRAWINGS

For a more complete understanding of the embodiments herein and the advantages thereof, reference is now made to the following descriptions taken in conjunction with the accompanying drawings, in which:

FIG. 2 is a side cross-sectional view of the tissue evacuation device of FIG. 1.

FIG. 3 is a detailed side cross-sectional view of the distal portion of the tissue evacuation device of FIG. 1.

FIG. 4 is a detailed side cross-sectional view of the proximal portion of the tissue evacuation device of FIG. 1.

FIG. 5 is a front cross-sectional view of the tissue evacuation device of FIG. 4 taken along line 5-5.

FIG. 6 is a side view of another embodiment of a tissue evacuation device.

FIG. 7 is a side cross-sectional view of the tissue evacuation device of FIG. 6.

FIG. 8 is a detailed side cross-sectional view of the distal portion of the tissue evacuation device of FIG. 6.

DETAILED DESCRIPTION OF THE INVENTION

Figure 1:
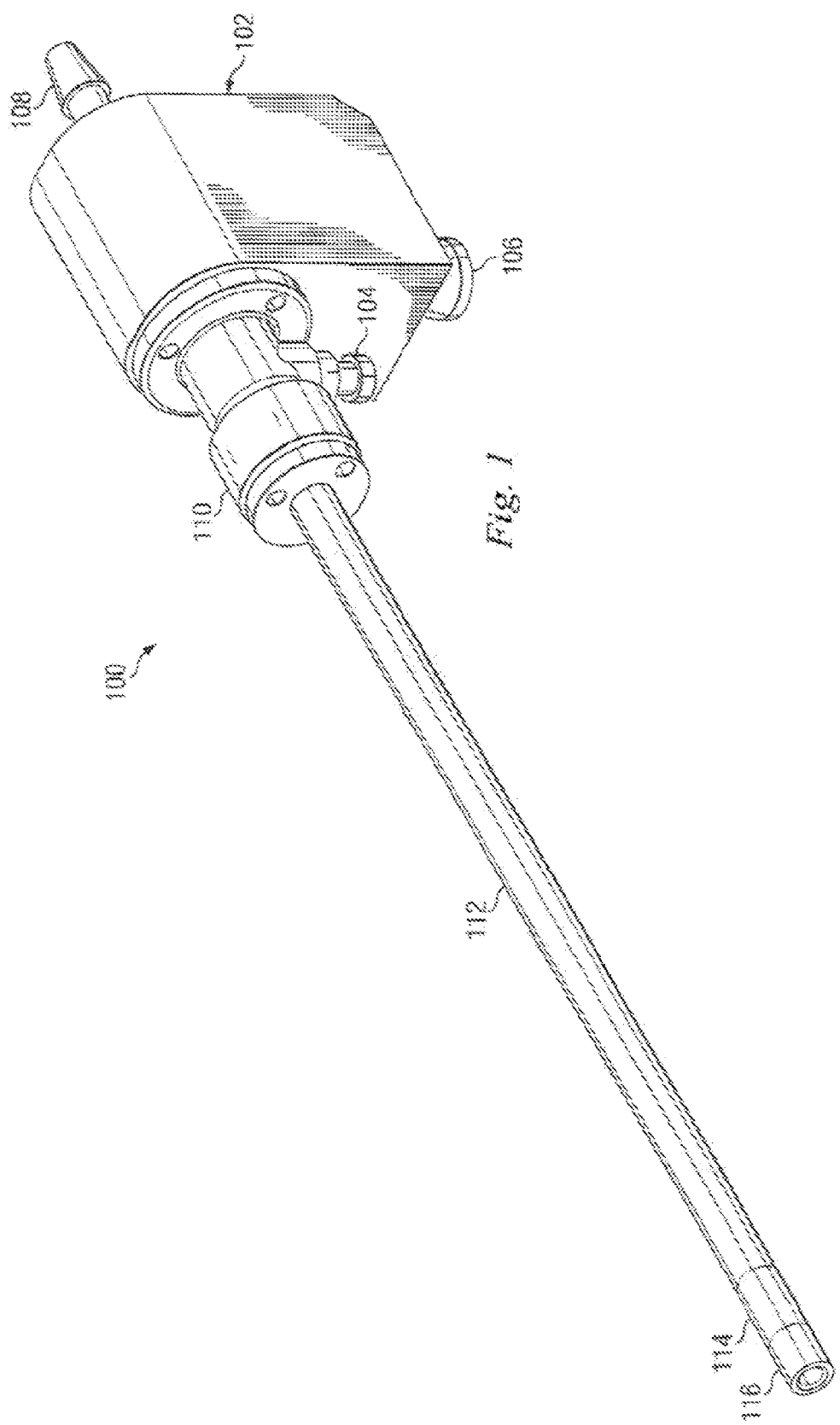
FIG. 1 is a perspective view of one embodiment of a tissue evacuation device.

In the following discussion, numerous specific details are set forth to provide a thorough understanding of the present invention. However, those skilled in the art will appreciate that the present invention may be practiced without such specific details. Furthermore, it is understood that the following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring to FIG. 1, in one embodiment, a tissue evacuation device 100 is illustrated. The tissue evacuation device 100 may be designed to provide a high-energy fluid (e.g., a heated vapor) to targeted tissue for breaking down the targeted tissue, such as the nucleus of an intervertebral disc. After the nucleus or other targeted tissue is broken down, the tissue evacuation device 100 may also remove some or all of the broken down tissue.

The tissue evacuation device 100 may have an assembly housing 102 located on the proximal end of the device (from the perspective of a user) that may be used as a grip. The assembly housing 102, which will be discussed in greater detail with respect to FIG. 4, may include one or more external connectors (i.e., fittings or couplings) for supplying power, fluid, and/or pressure to the tissue evacuation device 100. In the present example, such connectors may include a fluid connector 104, a power (electrical) connector 106, and a vacuum connector 108.

The assembly housing 102 may be coupled to a collar attachment 110 that couples the assembly housing 102 to an outer tube 112. The outer tube 112 may serve as a device extension cannula to provide access for the high-energy fluid into tissue such as the nucleus. An evaporation chamber portion 114, which may be separate from or integral with the outer tube 112, may be positioned near the distal end of the outer tube 112. As will be described later in greater detail, the evaporation chamber 114 is where a fluid provided to the tissue evacuation device 100 may transition from a liquid state to a high-energy vapor state. A nozzle 116 may be located at the distal end of the outer tube 112 and may be configured to provide the high-energy vapor to the targeted tissue via one or more channels. In the present example, the nozzle 116 may include a vacuum opening for the evacuation of tissue.

Referring to FIG. 2, a cross-sectional view of the tissue evacuation device 100 of FIG. 1 is illustrated. Each portion of the tissue evacuation device is described below in greater detail, and so is not described with respect to the present figure. More specifically, the distal section (encompassing the evaporation chamber 114 and the nozzle 116) is described with respect to FIG. 3 and the proximal section (encompassing the assembly housing 102 and collar attachment 110) is described with respect to FIG. 4.

Referring to FIG. 3, the distal section of FIG. 2 is enlarged to illustrate a cross-sectional view of the outer tube 112, evaporation chamber 114, and nozzle 116 in greater detail. In the present example, the outer tube may be formed at least partially of an electrically conductive material (e.g., a metal). The conductive material of the outer tube 112 may be relatively thin from the assembly housing 102 until it nears the distal portion of the outer tube 112 where the evaporation chamber 114 is located. At this point, the conductive material may be thicker to form an electrode 307. Alternatively, the conductive material forming the outer tube 112 may be a single thickness throughout and/or may connect to an electrode (e.g., the electrode 307) that is not formed from the outer tube 112. It is understood that, in some embodiments, the outer tube 112 may contain no conductive material and other means (e.g., a wire integrated into or running along the outer tube) may be used for transferring voltage to the distal end of the tissue evacuation device 100.

An inner tube 302 may be positioned within the outer tube 112. In the present example, the exterior of the inner tube 302 may be approximately equidistant from the interior of the outer tube 112 (e.g., the inner and outer tubes are concentric circles), but other configurations may be used. Like the outer tube 112, the inner tube 302 may also be formed at least partially from a conductive material. The interior of the inner tube 302 may be substantially hollow and may provide a path for a vacuum between the distal end of the tissue evacuation device 100 and the assembly housing 102. An outer electrode wire 304 may connect the outer tube 112 (or the conductive portion of the outer tube) to a power source.

Insulation material 308 may be positioned between the inner tube 302 and outer tube 112 for at least a portion of the length of each tube, and may stop at approximately the evaporation chamber 114. The insulation material 308 may minimize or prevent electrical current from moving between the electrodes formed by the outer tube 112 and inner tube 302 when voltage is applied to the outer electrode wire 304 and an inner electrode wire 407 (FIG. 4).

One or more fluid spaces 310 may be provided within the evaporation chamber 114. The fluid space 310 may be connected to the fluid connector 106 of the assembly housing 102 via a channel or conduit 312 positioned between the inner tube 302 and outer tube 112. It is understood that the conduit 312 may form part of the fluid space 310 or may be separated from the fluid space (e.g., by a valve or other fluid control means).

A porous material 314 may be positioned proximate to the conductive material of the inner tube 302 and outer tube 112. It is noted that the insulation material 308 may be positioned so as not to insulate the area covered by the porous material 314. The porous material 314, which may be a ceramic open-cell porous material, may be positioned within or coupled to the fluid space 310 and may serve as a capillary fluid container. Accordingly, fluid from the fluid space 310 may enter the porous material 314. The porous material 314 may be selected to accommodate various requirements, such as reducing arcing that may occur between the inner tube 302 and outer tube 112 when voltage is applied.

The nozzle 116 may include one or more vapor conduits 316 coupling the evaporation chamber (e.g., the porous material 314) with one or more nozzle holes 318. The particular configuration of the nozzle 116 may vary. For example, a single vapor conduit 316 may be coupled to multiple nozzle holes 318, multiple vapor conduits may be coupled to a single nozzle hole, or there may be a one to one correspondence between the vapor conduits and the nozzle holes.

It is understood that the use of terms such as "evaporation chamber" and "nozzle" are for purposes of illustration through the present disclosure and are not meant to limit the present disclosure by requiring that certain components be positioned within a particular section. For example, some overlap may occur between the evaporation chamber and the nozzle and such overlap may depend largely on the particular embodiment of the tissue extraction instrument.

Referring to FIG. 4, the proximal section of FIG. 2 is enlarged to illustrate a cross-sectional view of the assembly housing 102 and collar attachment 110 in greater detail. As described previously, the assembly housing 102 may include the fluid connector 104, the electrical connector 106, and the vacuum connector 108. It is noted that the outer tube 112 may enter and be supported by the collar attachment 110 but may not extend into the assembly housing 102, while the inner tube 302 may extend through at least a portion of the assembly housing 102. An o-ring 402 may provide a seal between the collar attachment 110 and the outer tube 112. A shoulder 404 may provide an attachment flange for outer tube 112. For example, the shoulder 404 may have a fitting that couples to outer tube 112 or the shoulder 404 may be welded to outer tube 112 and then attached to collar attachment 110. The collar may be removable and, in some embodiments, may contain fastening mechanisms that allow for the attachment and detachment of the outer tube 112 and/or other components.

The fluid connector 104 may couple an external fluid source 105 (as shown in FIG. 2) to the fluid space 310 via a valve 405 and the conduit 312 (FIG. 3). The fluid may be supplied as a liquid to the fluid space 310 and converted to a gas in the evaporation chamber 114. In some embodiments, the fluid connector 104 may include a tailored (e.g., barbed) fitting for connection.

The electrical connector 106 may provide power for a bipolar electrode set (positive and negative electrodes) formed from outer tube 112 and inner tube 302. More specifically, the electrical connector 106 may couple the outer electrode wire 304 to a power source to provide power to the outer tube 112. In the present embodiment, the outer electrode wire 304 may connect directly to the proximal end of the outer tube 112. The electrical connector 106 may also couple an inner electrode wire 407 to the power source to provide power to the inner tube 302. In the present embodiment, the inner electrode wire 407 may connect to a collar 406 that is coupled to the inner tube 302. The collar 406 may be conductive or may contain conductive elements that transfer voltage from the inner electrode wire 407 to the inner tube 302. In other embodiments, the inner electrode wire 407 may be coupled directly to the inner tube 302. Various wire fasteners/guides, such as a wire retainer 408 used for outer electrode wire 304, may be used to seal and/or support one or both of the inner and outer electrode wires.

The vacuum connector 108 may be coupled to the proximal end of the inner tube 302. An o-ring 410 may provide a seal between inner tube 302 and assembly housing 102. An o-ring 412 may provide a seal between inner tube 302 and collar attachment 110. In some embodiments, the vacuum connector 108 may include a tailored fitting (e.g., a barb) for connection to a vacuum system such as a surgical room suction system.

Although not shown, it is understood that various modifications may be made to the fluid, electrical, and vacuum portions of the tissue extraction device 100. For example, while the outer electrode wire 304 and inner electrode wire 407 are illustrated as connected (e.g., soldered or otherwise affixed) within the tissue extraction device 100, various means may be supplied to enable a user to engage and/or disengage a wire.

Referring to FIG. 5, a cross-sectional view of the assembly housing 102 of FIG. 5 along line 5-5 of FIG. 4 is illustrated. The fluid connector 104 and electrical connector 106 of housing assembly 102 are visible.

Referring to FIG. 6, in another embodiment, a tissue evacuation device 600 may include an assembly housing 602 located on the proximal end of the device (from the perspective of a user) that may be used as a grip. The assembly housing 602, which will be discussed in greater detail with respect to FIG. 9, may include one or more external connectors or fittings for supplying power, fluid, and/or pressure to the tissue evacuation device 600. In the present example, such connectors may include a fluid connector 604, a power (electrical) connector 606, and a vacuum connector 608.

The assembly housing 602 may be coupled to a collar attachment 610 that couples the assembly housing 602 to an outer tube 612. The outer tube 612 may provide a relatively rigid structure coupled to (or including) an evaporation chamber 614 and a nozzle 616. As will be described in greater detail below, the outer tube 612 in the present embodiment may not be included in a power circuit used to evaporate fluid. The evaporation chamber 614 may be where a fluid provided to the tissue evacuation device 600 may transition from a liquid state to a high-energy vapor state. The nozzle 616 may be located at the distal end of the outer tube 612 and may be configured to provide the high-energy vapor to the targeted tissue via one or more channels. In the present example, the nozzle 616 may include a vacuum opening for the evacuation of tissue.

Referring to FIG. 7, a cross-sectional view of the tissue evacuation device 600 of FIG. 6 is illustrated. Each portion of the tissue evacuation device is described below in greater detail, and so is not described with respect to the present figure. More specifically, the distal section (encompassing the evaporation chamber 614 and the nozzle 616) is described with respect to FIG. 8 and the proximal section (encompassing the assembly housing 602 and collar attachment 610) is described with respect to FIG. 9.

Referring to FIG. 8, the distal section of FIG. 7 is enlarged to illustrate a cross-sectional view of the outer tube 612, evaporation chamber 614, and nozzle 616 in greater detail. In the present example, the outer tube may provide an exterior structure but may not form part of the electrical circuit and, accordingly, may not be formed of an electrically conductive material (e.g., a metal). The outer tube 112 may vary in thickness or may be of a uniform thickness. It is understood that, in some embodiments, the outer tube 112 may include conductive material and be used to form part of an electrical circuit.

An inner tube 802 may be positioned within the outer tube 612. In the present example, the exterior of the inner tube 802 may be approximately equidistant from the interior of the outer tube 612 (e.g., the inner and outer tubes are concentric circles), but other configurations may be used. The inner tube 802 may be formed at least partially from a conductive material and may form an inner electrode that is part of an electrical circuit. The interior of the inner tube 802 may be substantially hollow and may provide a path for a vacuum between the distal end of the tissue evacuation device 600 and the assembly housing 602.

An outer electrode 804 may be electrically coupled to the assembly housing 602 by an outer electrode wire 806. The outer electrode wire 806 may be positioned between the outer tube 612 and the inner tube 802. Insulation material 808 may be used to cover the exterior of the outer electrode 804. In some embodiments, the outer tube 612 may extend over the outer electrode 804 and the insulation material 808 may be positioned between the outer electrode and the outer tube. In other embodiments, if the outer tube 612 extends over the outer electrode 804 and is not conductive, the insulation material 808 may not be present.

Insulation material 810 (e.g., a Teflon sleeve) may be positioned between the inner tube 802 and outer tube 612 for at least a portion of the length of each tube, stopping at approximately the evaporation chamber 614. The insulation material 810 may be used to electrically insulate the inner tube 802 from the outer electrode wire 806 and outer tube 612.

One or more fluid spaces 812 may be provided within the evaporation chamber 614. The fluid space 812 may be connected to the fluid connector 604 of the assembly housing 602 via a channel or conduit 814 positioned between the inner tube 802 and outer tube 612. It is understood that the conduit 812 may form part of the fluid space 810 or may be separated from the fluid space (e.g., by a valve or other fluid control means).

A porous material 816 may be positioned between the conductive material of the inner tube 802 and outer electrode 804. It is noted that the insulation material 810 may be positioned so as not to insulate the area covered by the porous material. The porous material 816, which may be a ceramic open-cell porous material, may be positioned within or coupled to the fluid space 812 and may serve as a capillary fluid container. Accordingly, fluid from the fluid space 812 may enter the porous material 816. The porous material 816 may be selected to accommodate various requirements, such as reducing arcing that may occur between the inner tube 802 and electrode 804 when voltage is applied.

The nozzle 616 may include one or more vapor conduits 818 coupling the evaporation chamber (e.g., the porous material 816) with one or more nozzle holes 820. The particular configuration of the nozzle 616 may vary. For example, a single vapor conduit 818 may be coupled to multiple nozzle holes 820, multiple vapor conduits may be coupled to a single nozzle hole, or there may be a one to one correspondence between the vapor conduits and the nozzle holes.

Figure 9:
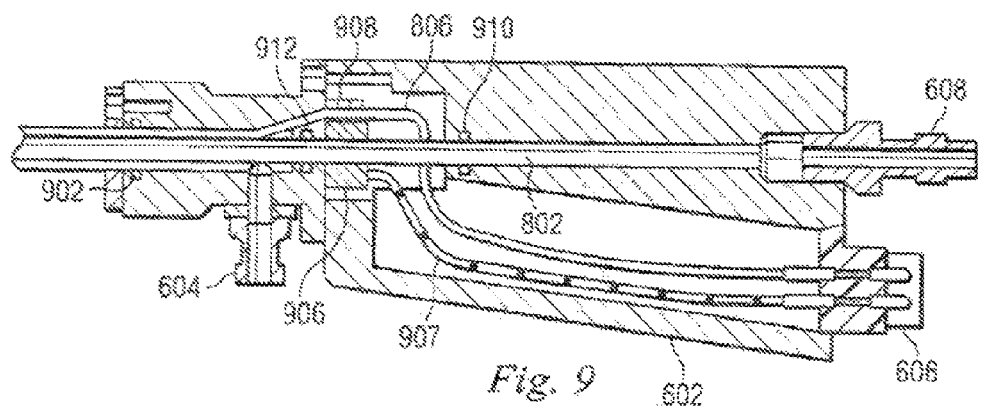
FIG. 9 is a detailed side cross-sectional view of the proximal portion of the tissue evacuation device of FIG. 6.

Referring to FIG. 9, the proximal section of FIG. 7 is enlarged to illustrate a cross-sectional view of the assembly housing 602 and collar attachment 610 in greater detail. As described previously, the assembly housing 602 may include the fluid connector 604, the electrical connector 606, and the vacuum connector 608. It is noted that the outer tube 612 may enter and be supported by the collar attachment 610 but may not extend into the assembly housing 602, while the inner tube 802 may extend through at least a portion of the assembly housing 602. An o-ring 902 may provide a seal between the collar attachment 610 and the outer tube 612. A shoulder 904 may provide an attachment flange for outer tube 612. For example, the shoulder 904 may have a fitting that couples to outer tube 612 or the shoulder 904 may be welded to outer tube 612 and then attached to collar attachment 610.

The fluid connector 604 may couple an external fluid source (not shown) to the fluid space 812 via a valve 905 and the conduit 814 (FIG. 8). The fluid may be supplied as a liquid to the fluid space 812 and converted to a gas in the evaporation chamber 614. In some, embodiments, the fluid connector 604 may include a tailored (e.g., barbed) fitting for connection.

The electrical connector 606 may provide power for a bipolar electrode set (positive and negative electrodes) formed from electrode 804 and inner tube 802. More specifically, the electrical connector 606 may couple the outer electrode wire 806 to a power source to provide power to the electrode 804. In the present embodiment, the outer electrode wire 806 may connect directly to electrode 804. The electrical connector 606 may also couple an inner electrode wire 907 to the power source to provide power to the inner tube 802. In the present embodiment, the inner electrode wire 907 may connect to a collar 906 that is coupled to the inner tube 802. The collar 906 may be conductive or may contain conductive elements that transfer voltage from the inner electrode wire 907 to the inner tube 802. In other embodiments, the inner electrode wire 907 may be coupled directly to the inner tube 802. Various wire fasteners/guides, such as a wire retainer 908 used for outer electrode wire 806, may be used to seal and/or support one or both of the inner and outer electrode wires.

The vacuum connector 608 may be coupled to the proximal end of the inner tube 802. An o-ring 910 may provide a seal between inner tube 802 and assembly housing 602. An o-ring 912 may provide a seal between inner tube 802 and collar attachment 610. In some embodiments, the vacuum connector 608 may include a tailored fitting (e.g., a barb) for connection to a vacuum system such as a surgical room suction system.

Although not shown, it is understood that various modifications may be made to the fluid, electrical, and vacuum portions of the tissue extraction device 600. For example, while the outer electrode wire 806 and inner electrode wire 907 are illustrated as connected (e.g., soldered or otherwise affixed) within the tissue extraction device 600, various means may be supplied to enable a user to engage and/or disengage a wire.

Figure 10:
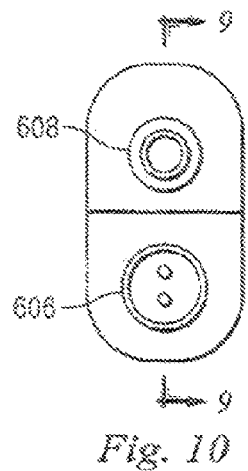
FIG. 10 is a front cross-sectional view of the tissue evacuation device of FIG. 6 taken along line 10-10.

Referring to FIG. 10, a cross-sectional view of the assembly housing 602 of FIG. 6 along lines 10-10 is illustrated.

Figure 11:
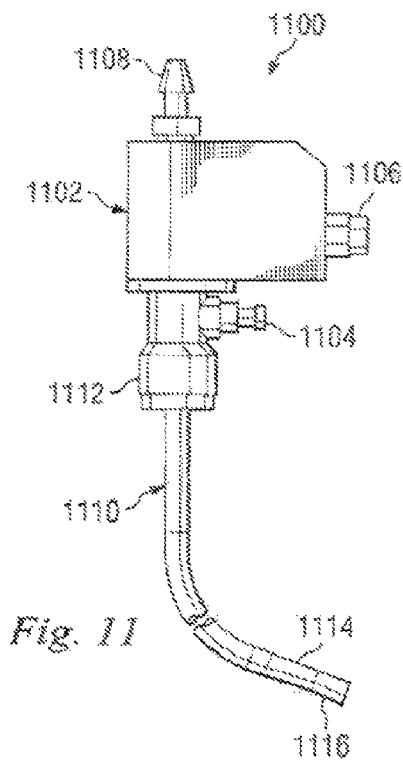
FIG. 11 is a side view of another embodiment of a tissue evacuation device.

Referring to FIG. 11, in another embodiment, a tissue evacuation device 1100 may include an assembly housing 1102 located on the proximal end of the device (from the perspective of a user) that may be used as a grip. The assembly housing 1102 may include one or more external connectors or fittings for supplying power, fluid, and/or pressure to the tissue evacuation device 1100. In the present example, such connectors may include a fluid connector 1104, a power (electrical) connector 1106, and a vacuum connector 1108. The assembly housing 1102 may be coupled to a tube 1110 via a collar 1112. The tube 1110 may extend from the assembly housing 1102 to an evaporation chamber 1114. A nozzle 1116 may be used to direct heated vapor from the evaporation chamber 1114 to a surgical site and may contain a vacuum opening coupled to the vacuum connector 1108. Although not shown, the tube 1110 may contain other components, such as an inner tube described with respect to other embodiments. Similarly, the evaporation chamber 1114 may be structured as has been described or may be constructed differently.

In the present example, the tube 1110 may be curved. The curve may be fixed or the tube 1110 may be articulating. Accordingly, a surgeon may control the movement of the tube 1110. For example, the surgeon may move the tube 1110 side to side or forward and backward to access the targeted tissue, as illustrated in FIG. 12.

Figure 12:
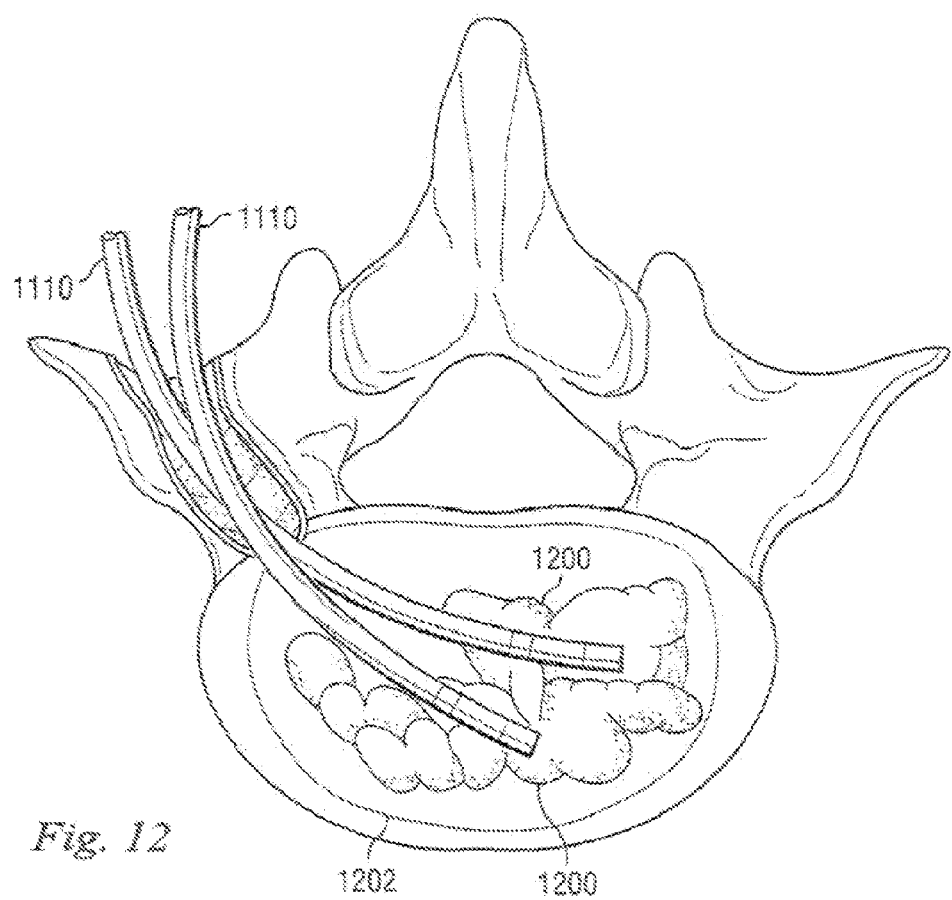
FIG. 12 is a diagram illustrating a portion of a tissue evacuation device removing nucleus tissue.

Referring to FIG. 12, a picture representation of a curved tube (e.g., the tube 1110 of the tissue evacuation device 1100 of FIG. 11) illustrates the removal of nucleus tissue 1200 from a spinal disc 1202. As shown in FIG. 12, the tube 1110 may provide access to nucleus tissue 1200 for a nuclectomy. In the present example, the tube 1110 may be inserted through the annulus to the nucleus tissue 1200. The tissue evacuation device 1100 may then break down the nucleus tissue 1200 using a heated vapor and remove at least a portion of the resulting debris from the spinal disc 1202. It is understood that, while FIG. 11 illustrates the tissue evacuation device 1100 removing nucleus tissue 1200, the tissue evacuation device 1100 may be used to remove other types of tissue.

Figure 13:
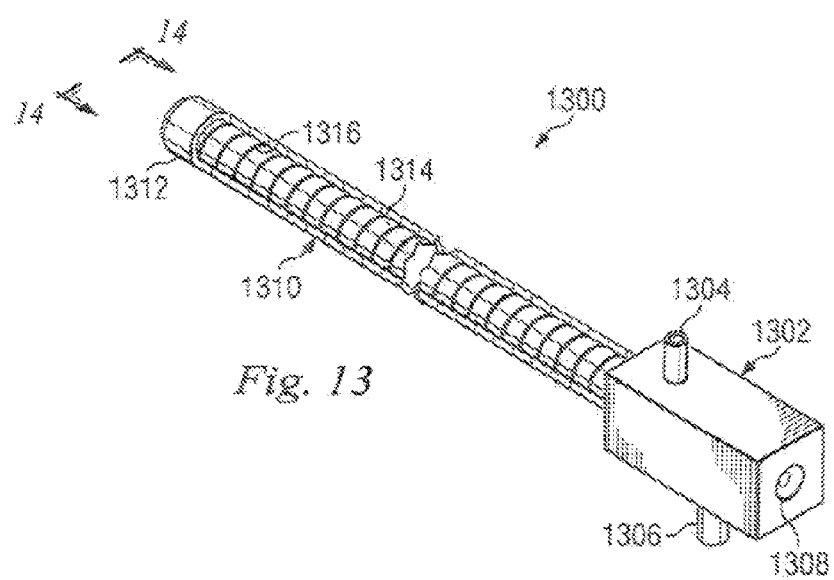
FIG. 13 is a perspective view of another embodiment of a tissue evacuation device.

Referring to FIG. 13, in another embodiment, a tissue evacuation device 1300 may include an assembly housing 1302 located on the proximal end of the device (from the perspective of a user) that may be used as a grip. The assembly housing 1302 may include one or more external connectors or fittings for supplying power, fluid, and/or pressure to the tissue evacuation device 1300. In the present example, such connectors may include a fluid connector 1304, a power (electrical) connector 1306, and a vacuum connector 1308. The assembly housing 1302 may be coupled to an outer tube 1310 that extends from the assembly housing to a nozzle 1312. As can be seen from the cross-sectional view provided by FIG. 13, the outer tube 1310 may contain an inner tube 1314 that provides support for a heating element 1316.

Figure 19:
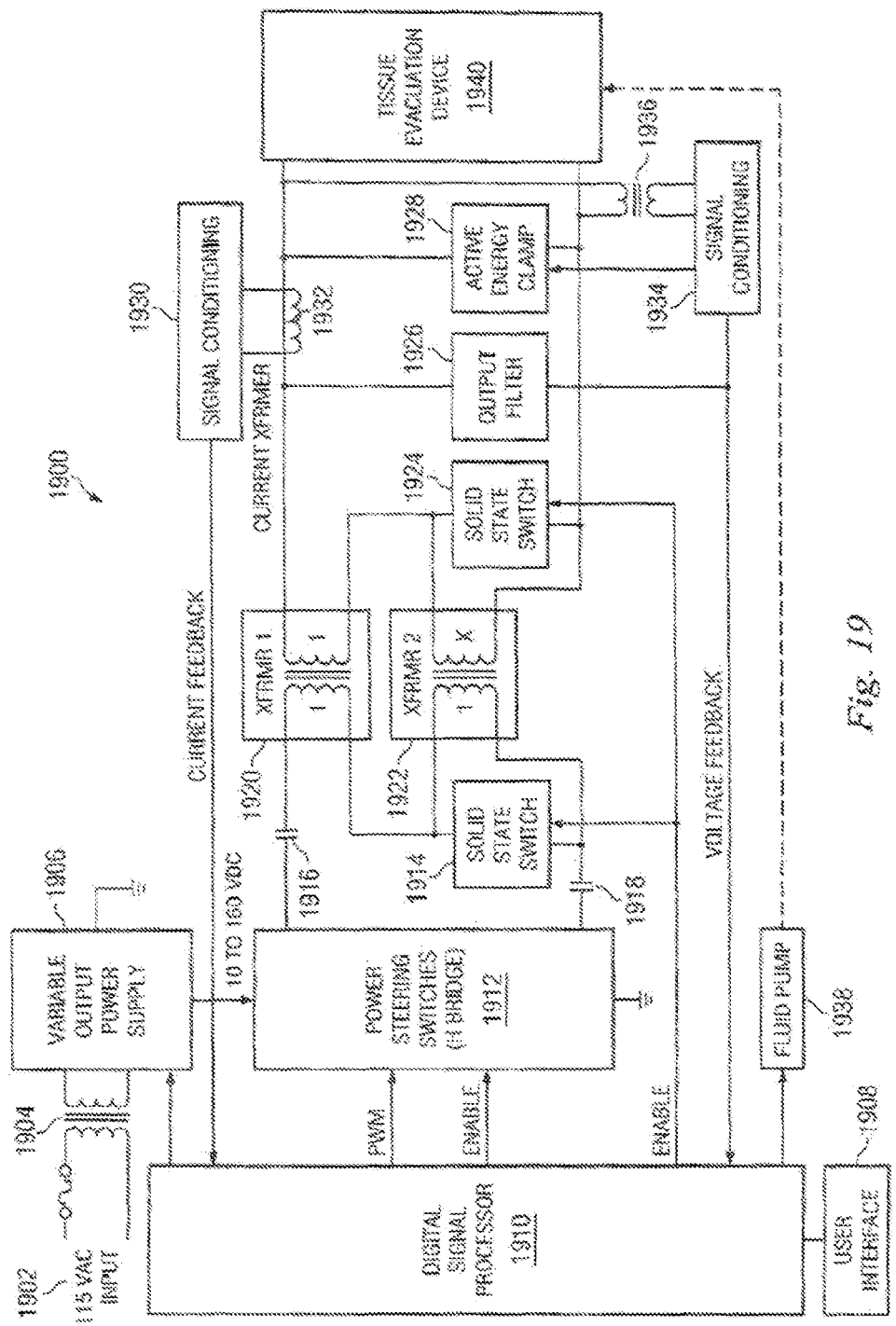
FIG. 19 is a diagram of one embodiment of a circuit that may be used to control a tissue evacuation device.

The power connector 1306 (e.g., heating wire leads) may provide a connection to an energy source (e.g., a variable impedance output RF generator such as that shown in FIG. 19) that may be used to provide the energy needed to move a fluid supplied via the fluid connector 1304 from a liquid state to a vapor state. The vacuum connector 1308 may be used to provide a negative pressure within the inner tube 1314 for removing small fragments of debris and droplets of condensed fluid (e.g., saline). The fluid connector 1304 may provide a fluid, such as water or saline solution, to the assembly housing 1302. The fluid connector 1304 may be configured to enable a user to control the inflow of the saline solution or other fluid into the assembly housing 1300.

Figure 14:
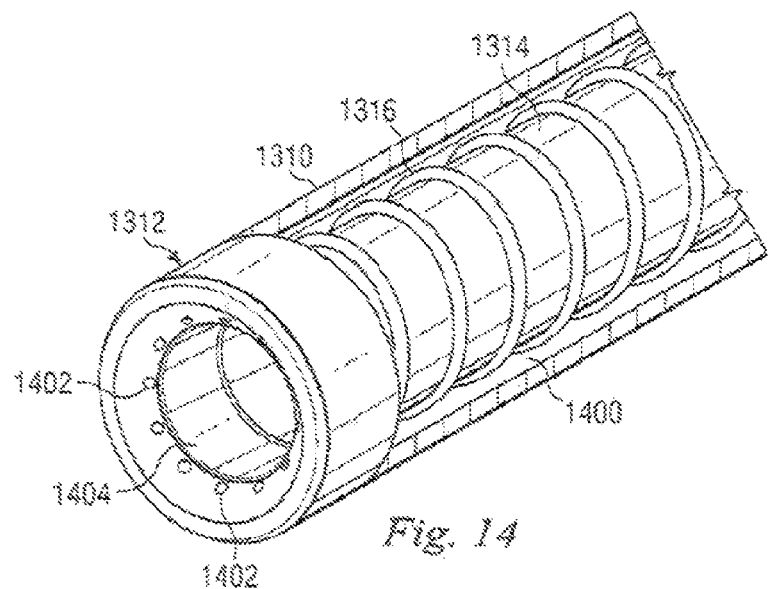
FIG. 14 is a cross-sectional view of the distal end of the tissue evacuation device of FIG. 13 taken along line 14-14.

With additional reference to FIG. 14, a more detailed embodiment of the distal end of the tissue extraction device 1300 of FIG. 13 is illustrated. The outer tube 1310 may surround the inner tube 1314. In the present embodiment, the heating element 1316 may be a single wire that is wrapped around the inner tube 1314. The heating element 1316 may be used to heat the fluid to varying temperatures based upon the voltage applied to the heating element. In other embodiments, multiple wires may be used. Furthermore, the wire or wires may be arranged differently (e.g., longitudinally down the length of the inner tube 1314 or each wire may be wrapped only partially around the inner tube). In other embodiments, the heating element 1316 may be supported by the outer tube 1310 rather than the inner tube 1314, or may be supported by both the outer and inner tubes.

A space 1400 may exist between the outer tube 1310 and inner tube 1314 to allow fluid to pass from the assembly housing 1302 to the nozzle 1312. As the fluid passes over the heating element 1316, it may vaporize and be discharged as vapor from the nozzle 1312 via nozzle ports 1402. A vacuum port 1404 in the nozzle 1312 may be coupled to the inner tube 1314 to couple the vacuum pressure supplied by the inner tube with the surgical site. Accordingly, when the nozzle 1312 is placed within the nucleus, the high temperature vapor may escape through the steam ports 1402 and break up the nucleus tissue, and debris and fluid may be removed from the nucleus via the vacuum port 1404.

It is understood that may different embodiments of this tissue extraction device 1300 may be envisioned. For example, an additional tube (not shown) may be provided between the outer tube 1310 and the inner tube 1314. This additional tube may be used to separate the heating element 1316 from the fluid that is to be vaporized. Heating of the additional tube by the heating element 1314 may then vaporize the fluid. Alternatively, multiple tubes (not shown) that extend at least part of the distance from the assembly housing 1302 to the nozzle 1312 may be positioned between the outer tube 1310 and inner tube 1314. Each tube may serve as a fluid conduit and the fluid may be vaporized by the heating element 1316. Alternatively, a separate heating element may be associated (e.g., wrapped around or running alongside) of each tube to provide for vaporization within the associated tube. Accordingly, control of fluid and/or heating of a particular tube may allow for additional user control. In some embodiments, each tube may be associated with a particular nozzle port 1402, which may provide for additional user control of the nozzle ports and/or amount of heated vapor used during a surgical procedure.

Figure 15:
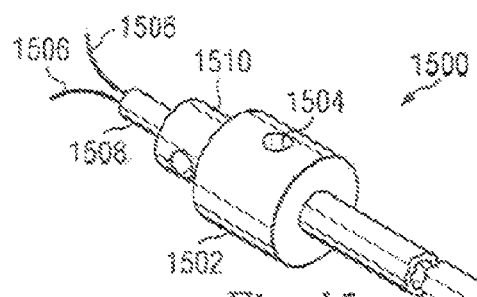
FIG. 15 is a perspective view of another embodiment of a tissue evacuation device.

Referring to FIG. 15, in still another embodiment, a tissue evacuation device 1500 may include an assembly housing 1502 located on the proximal end of the device (from the perspective of a user) that may be used as a grip. The assembly housing 1502 may include one or more external connectors or fittings for supplying power, fluid, and/or pressure to the tissue evacuation device 1500. In the present example, such connectors may include a fluid connector 1504, a power (electrical) connector 1506, a vacuum connector 1508, and a $CO_2$ connector 1510. The assembly housing 1502 may be coupled to an outer tube 1512 that extends from the assembly housing to a nozzle 1514. In the present example, the vacuum connector 1508 may be the proximal end of an inner tube that is surrounded by the outer tube 1512 between the assembly housing 1502 and the nozzle 1514.

The power connector 1506 (e.g., heating wire leads) may provide a connection to an energy source (e.g., a variable impedance output RF generator such as that shown in FIG. 19) that may be used to provide the energy needed to move a fluid supplied via the fluid connector 1504 from a liquid state to a vapor state. The vacuum connector and corresponding inner tube 1508 may be used to provide a negative pressure for removing small fragments of debris and droplets of condensed fluid (e.g., saline). The fluid connector 1504 may provide a fluid, such as water or saline solution, to the assembly housing 1502. The $CO_2$ connector may be coupled to a $CO_2$ tube (FIG. 16) that may be used to provide $CO_2$ gas for cooling the temperature of the vapor in the main tube 1512. It is understood that the use of $CO_2$ is for purposes of example and that other suitable fluids may be used in place of or in conjunction with $CO_2$.

Figure 16:
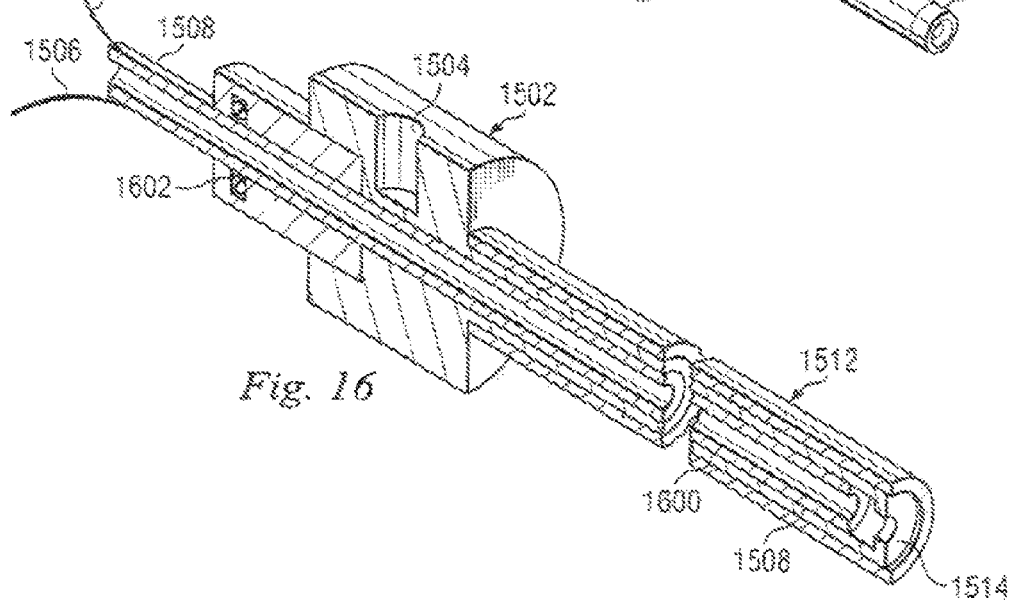
FIG. 16 is a cross-sectional view of the tissue evacuation device of FIG. 15.

Referring to FIG. 16, the tissue evacuation device of FIG. 15 is illustrated in cross-section. The outer tube 1512 may surround the inner tube 1508 and a $CO_2$ tube 1600 that is positioned between the outer and inner tubes. In the present example, the outer tube 1512, $CO_2$ tube 1600, and inner tube 1508 may be concentric cylinders. One or more heating elements (not shown) may be positioned between the assembly housing 1502 and the nozzle 1514 in the space between the outer tube 1512 and $CO_2$ tube 1600 and/or the space between the CO2 tube and the inner tube 1508. One or more o-rings, such as an o-ring 1602, may be used to provide a seal between components such as the inner tube 1508 and the $CO_2$ tube 1600.

It is understood that the connections between the various connectors and the spaces between the outer tube 1512 and $CO_2$ tube 1600 and between the $CO_2$ tube and the inner tube 1508 may vary, as may the location of the heating element(s). For example, in one embodiment, the fluid connector 1504 may supply fluid to the space between the outer tube 1512 and the $CO_2$ tube 1600, and the $CO_2$ connector 1506 may supply $CO_2$ to the space between the $CO_2$ tube and the inner tube 1308. The heating element may be positioned in the space between the inner tube 1508 and the $CO_2$ tube 1600 or between the outer tube 1512 and the $CO_2$ tube 1600. In another embodiment, the fluid connector 1504 may supply fluid to the space between the inner tube 1508 and the $CO_2$ tube 1600, and the $CO_2$ connector 1506 may supply $CO_2$ to the space between the $CO_2$ tube and the outer tube 1512. The heating element may be positioned in the space between the inner tube 1508 and the $CO_2$ tube 1600 or between the outer tube 1512 and the $CO_2$ tube 1600.

In another embodiment, a fluid such as $CO_2$ gas may be provided in the same cylindrical space as the heated vapor. For example, with respect to the tissue evacuation device 1300 of FIG. 14, the $CO_2$ gas may be injected into the space 1400 between the outer tube 1310 and inner tube 1314. In such an implementation, there may not be a separate $CO_2$ tube, such as the tube 1600 of FIG. 16.

Figure 17:
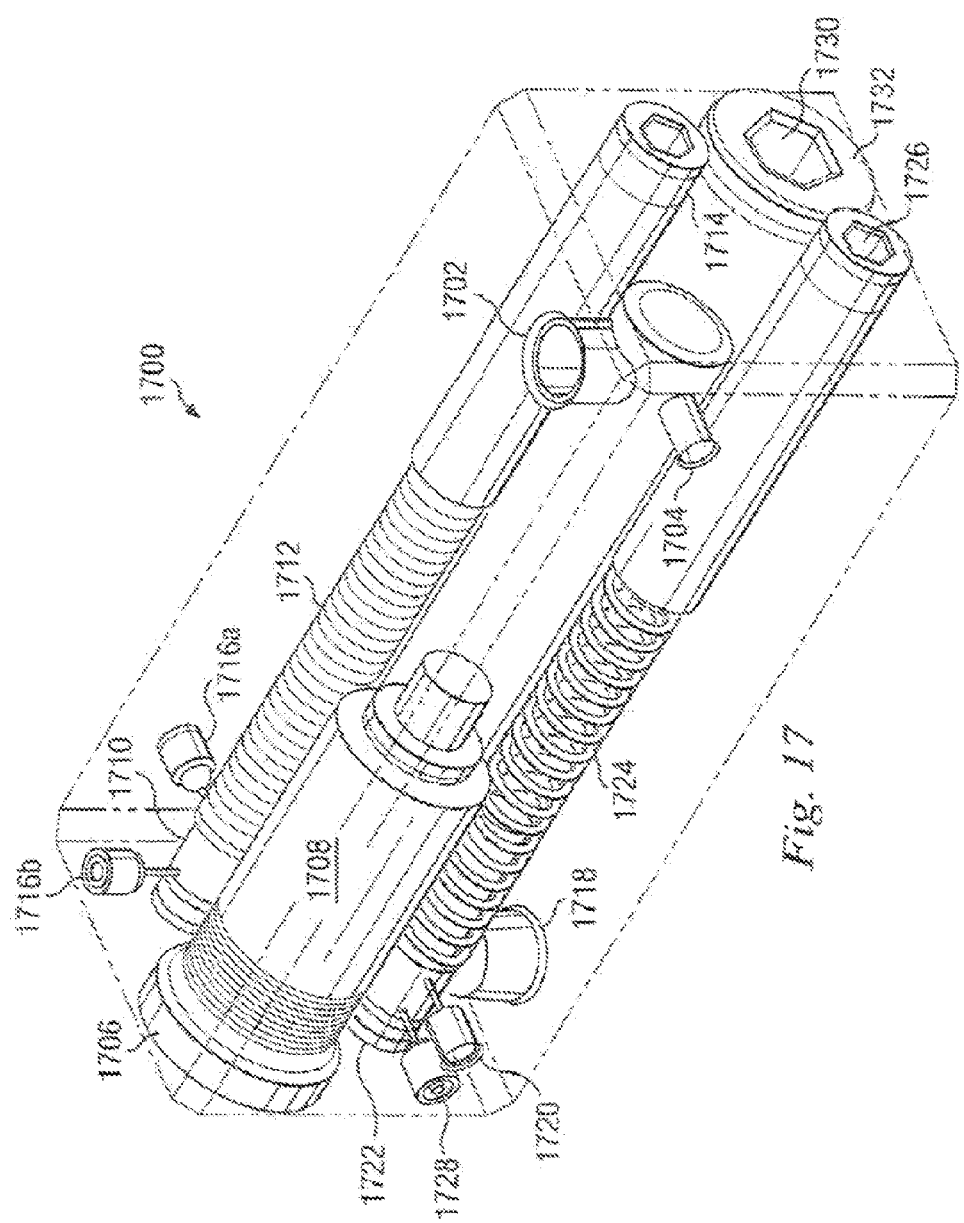
FIG. 17 is a perspective, cross-sectional view of one embodiment of an assembly housing that may be used with a tissue evacuation device.

Referring to FIG. 17, in one embodiment, an assembly housing 1700 is illustrated. The assembly housing 1700 may be configured for use with a tissue evacuation device such as those illustrated in FIGS. 13 and 15. In the present example, the assembly housing 1700 may be used to control the fluid (e.g., water) pressure and the $CO_2$ pressure in a tissue evacuation device. It is understood that the assembly housing 1700 may be connected to an energy source and controller to control the fluid intake and pressure and the $CO_2$ intake and pressure.

The water in the assembly housing 1700 may provided through a water port 1702. A water pressure gauge port 1704 may be used to measure the water pressure. A water cap 1706 may retain a water piston 1708 in the assembly housing 1700. A regulator piston 1710 and a water regulator spring 1712 may further assist with water pressure regulation. A water pressure regulator screw 1714 and two plugs 1716a and 1716b may be used to hold the regulator piston 1710 and the water regulator spring 1712 in place. The water regulator screw 1714 may enable the water pressure to be adjusted manually.

$CO_2$ in the assembly housing 1700 may be provided through a $CO_2$ port 1718. A $CO_2$ pressure gauge port 1720 may be used to measure the $CO_2$ pressure. A $CO_2$ regulator piston 1722 and a $CO_2$ regulator spring 1724 may assist with the $CO_2$ pressure regulation. A $CO_2$ pressure regulator screw 1726 and a plug 1728 may hold the $CO_2$ regulator piston 1722 and the $CO_2$ regulator spring 1724 in place. The $CO_2$ pressure regulator screw 1726 may enable the $CO_2$ pressure to be adjusted manually. A cartridge puncture screw 1730 may be used to control the $CO_2$ released from a $CO_2$ cartridge (FIG. 16). A $CO_2$ cap 1732 may be used in conjunction with the $CO_2$ regulator piston 1722 and the $CO_2$ regulator spring 1724 to control the $CO_2$ pressure.

Figure 18:
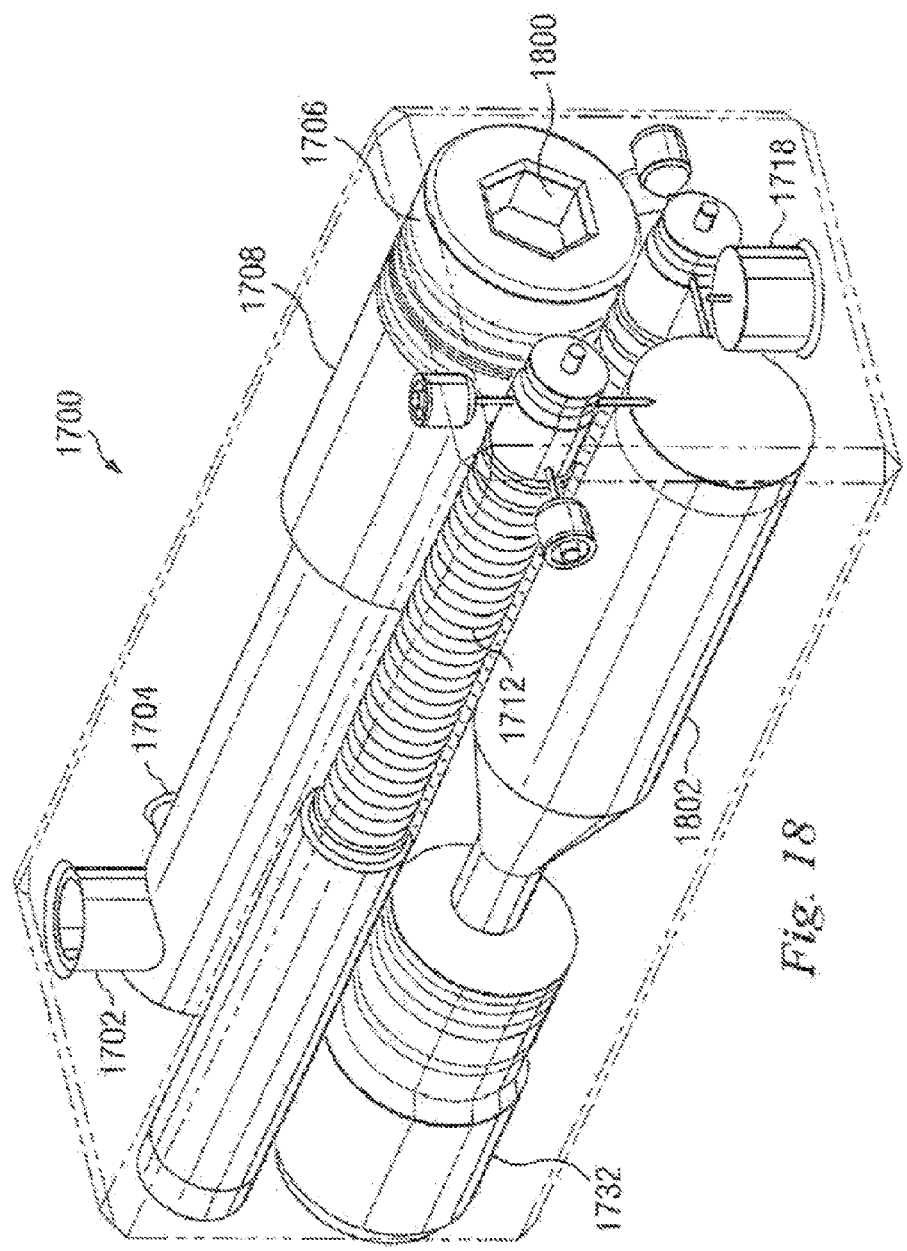
FIG. 18 is a perspective, cross-sectional view of the assembly housing of FIG. 17 taken along line 18-18.

Referring to FIG. 18, an alternate view along the lines 18-18 of the assembly housing 1700 of FIG. 17 is illustrated. As illustrated in FIG. 18, a water piston cap screw 1800 may be used to control the water piston 1708 and the corresponding water pressure. In the present embodiment, a $CO_2$ cartridge 1802 may be used to provide $CO_2$ to the assembly housing 1700 and the $CO_2$ port 1718 may be used to provide additional $CO_2$ beyond what is available in $CO_2$ cartridge 1802. In other embodiments, the $CO_2$ cartridge 1802 may not be implemented.

In operation, the assembly housing 1700 may be used to control the water pressure and $CO_2$ pressure for a tissue evacuation device. For example, with respect to the tissue evacuation device 1300 of FIG. 13, the assembly housing 1700 may be used to control the water or saline solution pressure in the main tube 1310. The water piston 1708, regulator piston 1710, and the regulator spring 1712 may work in conjunction to control the water pressure. The assembly housing 1700 may also be used with the tissue evacuation device 1300 to control the injection of $CO_2$ into the main tube 13 10. In this embodiment, the $CO_2$ gas and the steam may occupy the space 1400 (FIG. 14). As previously described, the $CO_2$ may be used to cool the heated saline vapor. The $CO_2$ cap 1732, $CO_2$ regulator piston 1722, $CO_2$ regulator spring 1724, and the $CO_2$ cartridge 1802 may work in conjunction to control the $CO_2$ pressure.

Additionally, in some embodiments, a vacuum tube (not shown) may be positioned within or coupled to the assembly housing 1700. In various embodiments, the vacuum tube may reside within the assembly housing 1700 or outside of the assembly housing 1700. In still other embodiments, one or more heating elements (not shown) may be positioned within the assembly housing 1700. In various embodiments, a heating element may heat the water or other fluid inside the assembly housing 1700 or outside of the assembly housing 1700.

Referring to FIG. 19, one embodiment of a variable impedance output RF circuit 1900 is illustrated. The circuit 1900 may be used as an energy source for a tissue evacuation device to vaporize a fluid such as water or saline solution. It is understood that a tissue evacuation device is not limited to the energy source provided by the variable impedance output RF circuit 1900, and that the circuit 1900 is only provided as an illustration of one possible energy source.

In the present example, the circuit 1900 may be coupled to a tissue evacuation device 1940 (e.g., to the assembly housing of such a device). The tissue evacuation device may be similar to those described previously (e.g., the tissue evacuation device 1300 of FIG. 13). As described above, various embodiments of a tissue evacuation device may convert a fluid to a heated vapor state. Accordingly, the circuit 1900 illustrates one embodiment of a circuit that may be used to supply and control the energy used to create the heated vapor.

A user interface 1908 may be used by a user to program a digital signal processor (DSP) 1910 to desired specifications (e.g., pressure, temperature, flow rate, and duration). The DSP 1910 may control, monitor, and measure one or more variables within the circuit 1900 and/or the tissue evacuation device 1940. An AC input voltage 1902 may supply a primary set of coils of a transformer 1904. A secondary set of coils of the transformer 1904 may be connected to a variable output power supply 1906. The variable output power supply 506 may convert the AC input voltage 1902 into a variable DC voltage. The DSP 1910 may control the variable output power supply 1906 to produce a specific DC voltage. In the present embodiment, the voltage ranges from approximately ten volts to approximately 160 volts DC.

The DC voltage may be applied to power steering switches (e.g., an H bridge) 1912. This DC voltage may control the amplitude of the output power. The power steering switches 1912 may form an inverter circuit to convert a DC voltage input into a RF AC output. Accordingly, the DSP 1910 may supply the power steering switches 1912 with a pulse width modulated ("PWM") signal and an enable signal. The PWM signal may provide the frequency of the RF AC output and the enable signal may turn the power steering switches 1912 on and off.

The power steering switches 1912 may supply voltage to two transformers 1920 and 1922. Capacitors 1916 and 1918 may be connected to the primary windings of transformer 1920 and transformer 1922, respectively. A solid state switch 1914 may be connected to the primary of coils of transformer 1922, and another solid state switch 1924 may be connected to the secondary set of coils of transformer 1922. An enable signal from the DSP 1910 may turn the solid state switches 1914 and 1924 on and off. The transformers 1920 and 1922 may be used to drive various impedance loads. In the present embodiment, transformer 1920 may have a low value windings ratio (e.g., 1:1) that may drive a low impedance load. Transformer 1922 may have a higher value windings ratio (e.g., 1:X) that may effectively develop a higher output voltage to drive a relatively high impedance load.

An output filter 1926 may filter the output of the transformers 1920 and 1922 to provide a relatively precise AC output. An active energy clamp 1928 may limit output power on detection of a voltage spike to prevent high voltages at the tissue evacuation device 1940. The RF AC output may be supplied to the tissue evacuation device 1940 to heat the pressurized fluid (e.g., water or saline solution). Accordingly, a fluid pump 1938 may supply the water or saline solution to the tissue evacuation device 1940 at a controlled rate. The DSP 1910 may control the liquid leaving the fluid pump 1938.

A signal conditioning block 1930 and a current transformer 1932 may provide the output current of the transformers 1920 and 1922 to the DSP 1910. A signal conditioning block 1934 and a transformer 1936 may provide the output voltage of the transformers 1920 and 1922 to the DSP 1910. These two mechanisms may provide a current feedback and a voltage feedback, respectively. This enables the DSP 1910 to read the output currents and voltages and adjust the variables of the RF generator circuit 1900 accordingly.

In this embodiment, the low impedance transformer 1920 may always be in the circuit and the high impedance transformer 1922 may be either in series with the first transformer 1920 or may be effectively shorted out of the circuit by the solid state switches 1914, 1924. The DSP 1910 may control the solid state switches 1914, 1924. The circuit 1900 may have the capability to drive the initial low impedance load (transformer 1920) effectively with the high impedance load (transformer 1922) removed from the circuit. Then, at an appropriate time, the high impedance output transformer 1922 may be switched into the circuit, which may allow efficient energy transfer to the high impedance load. When the transformer 1922 is short circuited, two separate magnetic paths may be provided for the different windings to prevent unnecessary high circulating currents in the windings of the transformer 1922.

In the present embodiment, the state of the process may be estimated by calculating the electrical impedance of the load. For example, the circuit 1900 may have the capability to monitor input voltage, output current, and output voltage through the DSP 1910. These parameters may be utilized to calculate the process state and determine the proper settings for power input, fluid flow rate, and output impedance. The desired process state may be input by a user via the user interface 1908. Such monitor mechanisms may be electrically insulated from the high voltage output to allow a patient safe isolated output.

Figure 20:
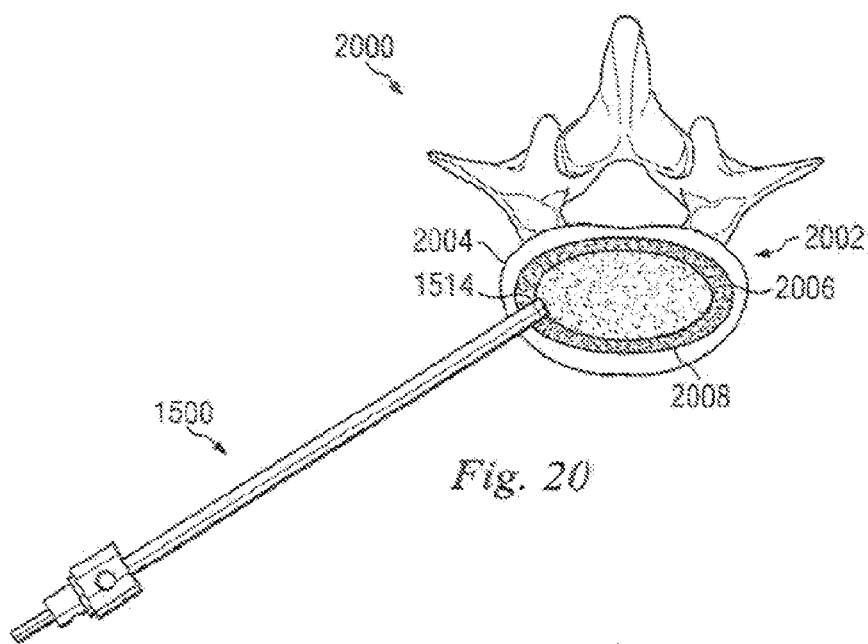
FIG. 20 is a diagram illustrating a tissue evacuation device removing nucleus tissue.

Referring to FIG. 20, a diagram 2000 illustrates a tissue evacuation device (e.g., the tissue evacuation device 1500 of FIG. 15) removing nucleus tissue 2006. The tissue evacuation device 1500 may be inserted into an intervertebral disc 2002 that resides between a vertebra 2004 and another vertebra (not shown) in the human spine. The intervertebral disc 2002 may include nucleus tissue 2006 surrounded by annulus tissue 2008. The nucleus tissue 2006 may have a lower collagen content than the surrounding annulus tissue 2008, and may be broken up with less energy than the annulus. A nozzle 1314 may be placed proximate to the nucleus tissue 2006. A heated vapor, such as steam, having a proper temperature and pressure may be directed into the nucleus tissue 2006 through steam ports (not shown) in the nozzle 1314. A vacuum may then be applied through the nozzle 1314 to remove at least a portion of the vaporized nucleus tissue and the condensed fluid from the steam. In the present example, the temperature and pressure of the steam is selected to have minimal impact on the annulus 2008. A circuit, such as the variable impedance output RF generator circuit 1900 of FIG. 19, may be used to adjust the temperature and pressure of the steam to remain within the desired range.

Figure 21:
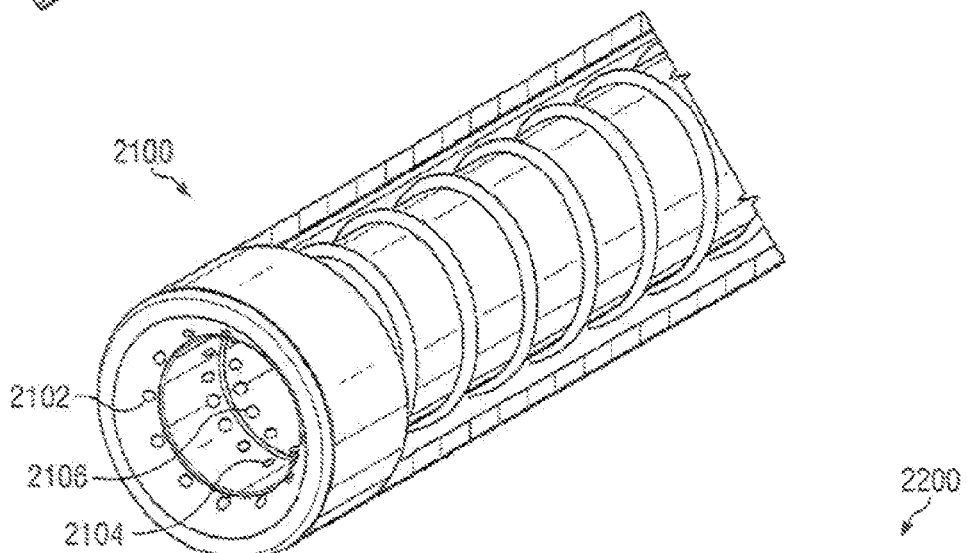
FIG. 21 is a perspective view of one embodiment of a nozzle that may be used with a tissue evacuation device.

Referring to FIG. 21, one embodiment of a nozzle 2100 that may be used with a tissue evacuation device, such as the tissue evacuation device 1300 of FIG. 13, is illustrated. The nozzle 2100 may include a first set of ports 2102 proximal to the end of the nozzle and at least a second set of ports 2104 positioned further back in the nozzle from the first set of ports. The first and second port sets 2102 and 2104 may be separated by a linear distance. In the present example, a third set of ports 2106 may also be provided. Each set of ports 2102, 2104, and 2106 may be positioned around the axis of a tube. While the present embodiment illustrates the ports of each set 2102, 2104, and 106 as being evenly distributed around the axis, it is understood that such a distribution is not necessary and the sets of ports, or even individual ports, may be distributed in many different ways.

In the present embodiment, the second and third sets of ports 2104 and 2106 may aid in minimizing or preventing the nozzle 2100 from becoming clogged during a surgical procedure. For example, the nozzle 2100 may become clogged as debris is vacuumed back to the assembly housing. The nozzle sets 2104 and 2106 may serve to further break down the debris as it passes through the nozzle and into the vacuum tube, which may minimize or prevent such clogging.

In some embodiments, the different sets of ports 2102, 2104, and 2106 (or even different ports in a single set) may be coupled to different vapor conduits (e.g., the vapor conduits 316 of FIG. 3). Accordingly, the particular configuration of the ports sets 2102, 2104, and 2106 may vary. For example, a single vapor conduit 316 may be coupled to multiple ports, multiple vapor conduits may be coupled to a single port, or there may be a one to one correspondence between the vapor conduits and the ports. Furthermore, vapor conduits may be shared among sets of ports. In addition, the division of ports into sets as shown is for purposes of illustration only, and ports may be individually placed in many different patterns.

Figure 22:
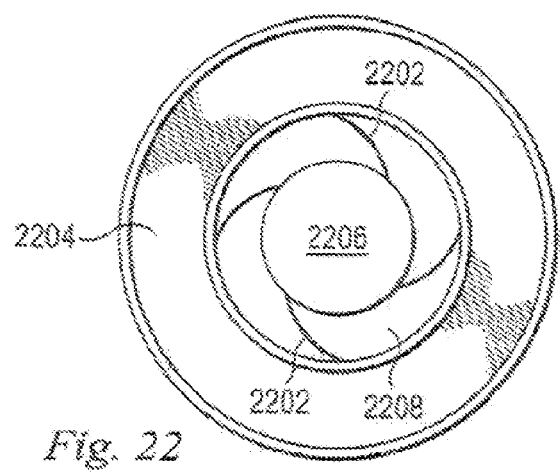
FIG. 22 is a perspective view of another embodiment of a nozzle that may be used with a tissue evacuation device.

Referring to FIG. 22, in another embodiment, a nozzle 2200 is illustrated that may be used with a tissue evacuation device, such as the tissue evacuation device 1300 of FIG. 13. The nozzle 2200 may include ports 2202 that may be positioned around the axis of a tube. A front surface 2204 of the nozzle 2200 may include an opening or bore 2206 and an inner portion 2208 extending outwardly from the bore. In some embodiments, the inner portion 2208 or the entire front surface 2204 may be conical. As described previously, the bore 2206 may be coupled to a vacuum source (not shown) and the ports 2202 may be coupled to a source (not shown) for steam or another heated gas. In the present example, each port 2202 may be a slot that curves in a spiral manner from an inner diameter of the inner portion 2208 (e.g., near the bore 2206) towards an outer diameter that is farther from the bore. The spiral design may, for example, concentrate the force provided by the heated gas. While the present embodiment illustrates the ports 2202 as being evenly distributed around the bore 2206, it is understood that other distributions may be used.

Figure 23:
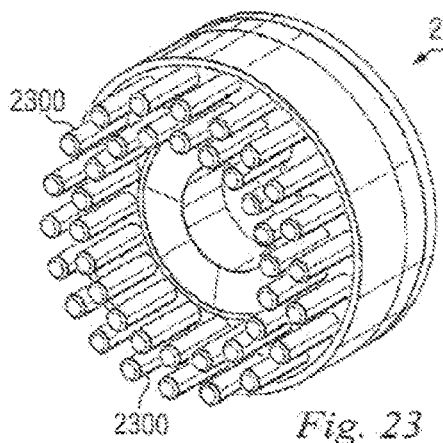
FIG. 23 is a perspective view of yet another embodiment of a nozzle that may be used with a tissue evacuation device.

Referring to FIG. 23, the nozzle 2200 of FIG. 22 is illustrated with a plurality of bristles or other extensions 2300 that may be used, for example, to scrape or dislodge tissue from an annulus. It is understood that the shape, height, and width of the bristles 2300, as well as the number of bristles, may be modified. Furthermore, the bristles 2300 may be rigid or somewhat flexible.

Figure 24:
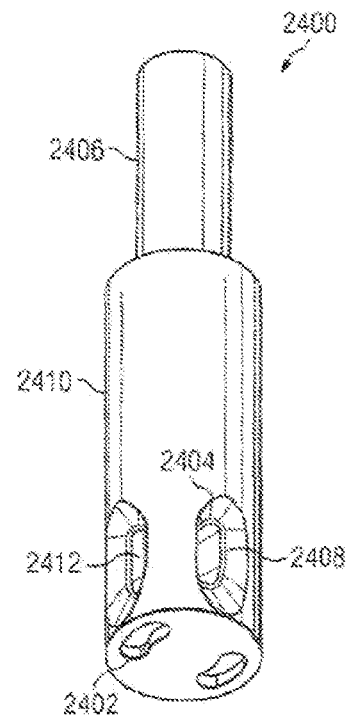
FIG. 24 is a perspective view of still another embodiment of a nozzle that may be used with a tissue evacuation device.

Referring to FIG. 24, in another embodiment, a nozzle 2400 is illustrated that may be used with a tissue evacuation device, such as the tissue evacuation device 1300 of FIG. 13. The nozzle 2400 may include front ports 2402 and side ports 2404 that may be positioned around the axis of a tube 2406, such as the outer tube 1310 of FIG. 13. Although both the front ports 2402 and side ports 2404 may be coupled to a source (not shown) for steam or another heated gas, some or all of the front ports 2402 or side ports 2404 may be coupled to a vacuum source (not shown). Alternatively, an inner housing 2408 may be coupled to a vacuum source or a heated gas source, while the front ports 2402 and side ports 2404 (positioned in an outer housing 2410) may be coupled to the source not coupled to the inner housing 2408. Slots or apertures 2412 in the inner housing 2408 may provide access for the vacuum or heated gas.

Figure 25A:
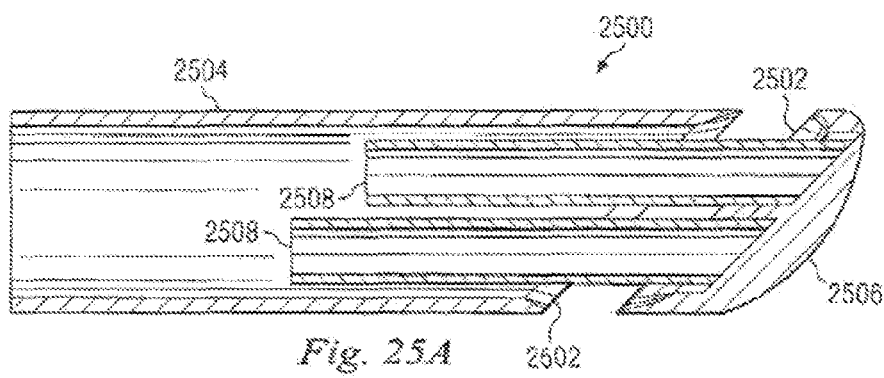
FIGS. 25A-25B are side and top views, respectively, of an embodiment of a scraper that may be used with a tissue evacuation device.
Figure 25B:
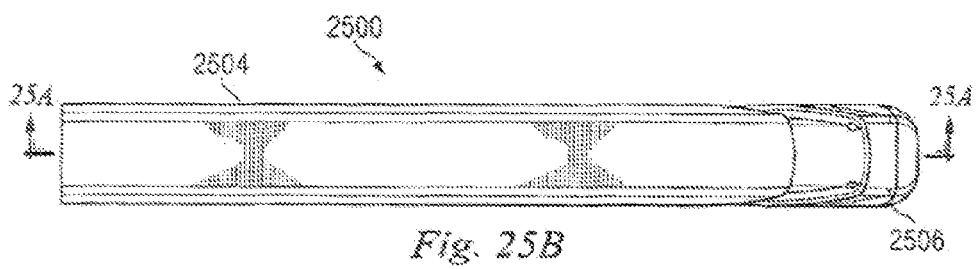

Referring to FIG. 25, in yet another embodiment, a scraper 2500 may be used with a tissue evacuation device, such as the tissue evacuation device 1300 of FIG. 13. For example, the scraper 2500 may be coupled to a distal end of the tissue evacuation device 1300. In the present example, the scraper 2500 may include one or more cutting edges 2502 positioned on a proximal portion 2504 and a distal portion 2506. Movement of the proximal portion 2504 and distal portion 2506 relative to one another may be achieved by one or more actuators 2508. Such movement may be used to remove tissue.

Other embodiments of a tissue evacuation device may include a surgical instrument having electrodes in a distal end of the instrument, such as:

1. A surgical instrument comprising:
    a housing;
    an outer tube having a first proximal end coupled to the housing and a first distal end;
    an inner tube having a second proximal end and a second distal end, wherein the inner tube is positioned within the outer tube and the second proximal end is coupled to the housing;
    a nozzle coupled to at least one of the first and second distal ends;
    first and second electrodes positioned opposite one another towards the first distal end between the nozzle and the first proximal end, wherein the first and second electrodes are separated by a porous material;
    a port connecting the porous material to the nozzle; and
    a liquid space positioned between the outer and inner tubes and coupled to the porous material and a liquid source.

2. The surgical instrument of embodiment 1 wherein the first electrode is formed by a portion of the outer tube that is made of a conductive material.

3. The surgical instrument of embodiment 2 wherein the second electrode is formed by a portion of the inner tube that is made of a conductive material.

4. The surgical instrument of embodiment 3 further comprising an insulation material positioned between the outer and inner tubes, wherein the insulation material is not present between the outer and inner tubes at a location of the first and second electrodes.

5. The surgical instrument of embodiment 4 wherein the inner tube is made entirely of a conductive material.

6. The surgical instrument of embodiment 5 wherein the housing includes:
    a conductive collar coupled to the inner tube; and
    an electrical conduit coupled to the collar.

7. The surgical instrument of embodiment 4 wherein the outer tube is made entirely of a conductive material.

The surgical instrument of embodiment 7 further comprising an insulation material covering an exterior surface of the outer tube.

9. The surgical instrument of embodiment 1 wherein the first electrode is positioned between the outer and inner tubes.

10. The surgical instrument of embodiment 9 wherein the second electrode is positioned between the outer and inner tubes.

11. The surgical instrument of embodiment 10 further comprising an insulation material positioned between the outer and inner tubes, wherein the insulation material is not present between the outer and inner tubes at a location of the first and second electrodes.

12. The surgical instrument of embodiment 1 wherein the housing includes:
    a connection for coupling a power supply to the first and second electrodes; and
    a connection for coupling the liquid source to the liquid space.

13. The surgical instrument of embodiment 12 wherein the housing further includes a connection for coupling the proximal end of the inner tube to a vacuum source.

14. A surgical instrument comprising:
    a housing;
    a first tube having a first proximal end coupled to the housing and a first distal end, wherein at least a portion of the first tube is electrically conductive and forms a first electrode;
    a second tube having a second proximal end and a second distal end, wherein the inner tube is positioned within the outer tube and the second proximal end is coupled to the housing, and wherein at least a portion of the second tube is electrically conductive and forms a second electrode positioned opposite the first electrode;
    a vaporization chamber formed of a porous material and positioned at least partially between the first and second electrodes and coupled to a gas conduit leading to a nozzle on the second distal end; and
    a liquid conduit configured to transport a liquid to the vaporization chamber.

15. The surgical instrument of embodiment 14 further comprising an insulation material positioned between the first and second tubes except for an area of the first and second tubes forming the first and second electrodes, respectively.

16. The surgical instrument of embodiment 14 wherein the housing includes:
    a connection for coupling a power supply to the first and second electrodes; and
    a connection for coupling the liquid source to the liquid conduit.

17. The surgical instrument of embodiment 16 wherein the housing further includes a connection for coupling the second proximal end to a vacuum source.

18. The surgical instrument of embodiment 14 wherein at least a portion of the second tube between the second electrode and the second proximal end is electrically conductive and wherein the housing includes:
    a conductive collar coupled to the second proximal end; and
    an electrical conduit coupled to the collar.

19. The surgical instrument of embodiment 14 further comprising an electrical conduit extending from the housing and coupled to the first electrode.

20. The surgical instrument of embodiment 19 wherein the electrical conduit is positioned between the first and second tubes.

21. The surgical instrument of embodiment 14 wherein the porous material reduces arcing between the first and second electrodes.

Other embodiments of a tissue evacuation device may include a surgical instrument having a heating element along a tube, such as:

1. A surgical instrument comprising:
    a housing;
    a first tube having a first proximal end coupled to the housing and a first distal end;
    a second tube having a second proximal end and a second distal end, wherein the second tube is positioned within the first tube and the second proximal end is coupled to the housing;
    a heating element positioned between the first and second tubes, wherein the heating element extends at least partially between the first proximal end and the first distal end;
    an electrical conduit extending from the housing and coupled to the heating element; and
    fluid conduit formed between the first and second tubes, wherein at least a portion of the fluid conduit is proximate to the heating element so that liquid within the fluid conduit can be vaporized.

2. The surgical instrument of embodiment 1 wherein the heating element is wrapped around the second tube in a spiral manner.

3. The surgical instrument of embodiment 1 wherein the heating element is coupled to an interior surface of the first tube.

4. The surgical instrument of embodiment 1 further comprising a nozzle coupled to the distal end of at least one of the first and second tubes, wherein the nozzle includes at least one exhaust port coupled to the fluid conduit.

5. The surgical instrument of embodiment 4 wherein the nozzle further includes an opening coupled to a bore extending the length of the second tube.

6. The surgical instrument of embodiment 5 wherein the housing includes a connection for coupling a vacuum source to the bore of the second tube.

7. The surgical instrument of embodiment 4 wherein the nozzle includes a plurality of exhaust ports.

8. The surgical instrument of embodiment 7 wherein the plurality of exhaust ports are equidistant from a vacuum opening in the center of the nozzle.

9. The surgical instrument of embodiment 7 wherein the plurality of exhaust ports are arranged in a spiral pattern centered on a vacuum opening in the center of the nozzle.

10. The surgical instrument of embodiment 4 wherein an exterior surface of the nozzle includes a plurality of bristles.

11. The surgical instrument of embodiment 1 further comprising a third tube positioned between the first and second tubes.

12. The surgical instrument of embodiment 11 wherein the heating element is positioned between the first and third tubes and the fluid conduit is positioned between the second and third tubes.

13. The surgical instrument of embodiment 11 wherein the heating element is positioned between the second and third tubes and the fluid conduit is positioned between the first and third tubes.

14. The surgical instrument of embodiment 1 wherein the housing includes:
a liquid port coupled to the fluid conduit, wherein the liquid port connects the fluid conduit to a liquid source; and
a liquid regulator mechanism to regulate liquid flow into the fluid conduit.

15. The surgical instrument of embodiment 14 wherein the housing further includes:
a gas port coupled to a gas conduit positioned between the first and second tubes, wherein the gas port connects the gas conduit to a gas source; and
a gas regulator mechanism to regulate gas flow into the gas conduit.

16. The surgical instrument of embodiment 15 wherein the gas conduit and the fluid conduit are the same conduit.

17. The surgical instrument of embodiment 15 further comprising a third tube positioned between the first and second tubes.

18. The surgical instrument of embodiment 17 wherein the gas conduit is positioned between the first and third tubes and the fluid conduit is positioned between the second and third tubes.

19. The surgical instrument of embodiment 17 wherein the gas conduit is positioned between the second and third tubes and the fluid conduit is positioned between the first and third tubes.

20. The surgical instrument of embodiment 1 wherein the housing includes a connection for coupling a power supply to the heating element.

21. A surgical instrument comprising:
a housing;
a first tube having a first proximal end coupled to the housing and a first distal end;
a second tube having a second proximal end and a second distal end, wherein the second tube is positioned within the first tube and the second proximal end is coupled to the housing;
a heating element positioned between the first and second tubes, wherein the heating element extends at least partially between the first proximal end and the first distal end;
an electrical conduit extending from the housing and coupled to the heating element;
a fluid conduit positioned within the first tube, wherein at least a portion of the fluid conduit is proximate to the heating element so that fluid within the fluid conduit can be vaporized.

22. The surgical instrument of embodiment 21 wherein the fluid conduit comprises at least a portion of a space between the first and second tubes.

23. The surgical instrument of embodiment 21 further comprising a third tube positioned within the first tube, wherein the fluid conduit is divided between the second and third tubes.

24. The surgical instrument of embodiment 23 wherein a first portion of the heating element is adjacent to the second tube and a second portion of the heating element is adjacent to the third tube.

25. The surgical instrument of embodiment 24 wherein the first and second heating element portions are separately controllable.

26. The surgical instrument of embodiment 23 wherein a fluid flow in each of the second and third tubes is separately controllable.

27. The surgical instrument of embodiment 21 wherein the housing includes:
a connection for coupling a power supply to the heating element; and
a connection for coupling a liquid source to the fluid conduit.

28. The surgical instrument of embodiment 21 wherein the housing includes a connection for coupling a vacuum source to a bore extending through the second tube.

29. An attachment for a surgical instrument comprising:
a distal portion having at least a first cutting edge on a proximal surface thereof,
a proximal portion configured for coupling to the surgical instrument, wherein a distal surface of the proximal portion includes a second cutting edge positioned to contact the first cutting edge when the distal and proximal portions are in contact; and
means for controlling a spacing between the distal and proximal portions, wherein the spacing includes a maximum distance and a minimum distance between the distal and proximal portions, and wherein the first and second portions are abutting at the minimum distance.

30. The attachment of embodiment 29 wherein the means for controlling includes at least one rod member extending from the proximal portion to the distal portion.

It is understood that the present invention can take many forms and embodiments. Accordingly, several variations of the present design may be made without departing from the scope of the invention. The capabilities outlined herein allow for the possibility of a variety of models. This disclosure should not be read as preferring any particular model, but is instead directed to the underlying concepts on which these models can be built. For example, although circular tubes are illustrated in the present disclosure, the tubes discussed in the present disclosure may be any shape. In addition, components described with respect to one embodiment may be used in place of or in addition to components described with respect to another embodiment. Furthermore, it is understood that terms such as "side", "top", "bottom", "front", "back", "proximal", and "distal" are relative and may be interchangeable depending on the perspective from which the device of the present disclosure is being viewed. Also, some features may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

I claim:

1. A surgical instrument for tissue extraction comprising:
   an elongated introducer body extending along an axis to a distal end;
   a passageway extending through the elongated introducer body including a proximal end and a distal opening; wherein the distal opening is configured with an inwardly sloping surface that transitions to the passageway;
   a plurality of flow outlets positioned in the inwardly sloping surface; and
   an evaporation chamber located adjacent to the distal opening, where the evaporation chamber is in fluid communication with a fluid source to convert a fluid to a vapor such that the vapor exits through the plurality of flow outlets.

2. The surgical instrument of claim 1 wherein the plurality of flow outlets are positioned around said inwardly sloping surface.

3. The surgical instrument of claim 2 wherein said plurality of flow outlets are positioned equidistantly around said inwardly sloping surface.

4. The surgical instrument of claim 1 further comprising at least one passage within a wall of the elongated introducer body in fluid communication with the plurality of flow outlets.

5. The surgical instrument of claim 4 wherein the fluid source is operatively coupled to the at least one passage.

6. The surgical instrument of claim 1 wherein the fluid source is a water vapor source positioned within said wall for providing a flow of water vapor through the plurality of flow outlets.

7. The surgical instrument of claim 6 wherein the water vapor source comprises at least first and second radiofrequency (RF) electrodes.

8. The surgical instrument of claim 1 wherein the plurality of flow outlets are configured to direct flows therethrough in converging paths.

9. The surgical instrument of claim 1 wherein the at least one passage is proximate to the plurality of flow outlets and is configured direct a flow toward said axis.

10. The surgical instrument of claim 1 further comprising a vacuum source operatively coupled to the proximal end of the passageway.

11. A surgical instrument for tissue extraction using a high energy fluid, the surgical instrument comprising:
    an elongated introducer body extending along an axis to a distal end, a portion of the elongated introducer body being fluidly coupleable to a source of fluid;
    an inner tube defining a passageway extending through the elongated introducer body, the passageway including a proximal end and a distal opening; wherein the distal opening is configured with an inwardly sloping surface that transitions to the passageway, where the proximal end of the passageway is fluidly coupleable to a vacuum source;
    a chamber having a heating element, where the chamber is located exterior to the inner tube and interior to the elongated introducer body and adjacent to the distal opening, where the heating element can transform fluid passing through the chamber into the high energy fluid, and
    a plurality of flow outlets positioned in the inwardly sloping surface, where the plurality of flow outlets are in fluid communication with the chamber.

12. The surgical instrument of claim 11 wherein the plurality of flow outlets are positioned around said inwardly sloping surface.

13. The surgical instrument of claim 12 wherein said plurality of flow outlets are positioned equidistantly around said inwardly sloping surface.

14. The surgical instrument of claim 11 further comprising at least one passage within a wall of the elongated introducer body in fluid communication the chamber and with the plurality of flow outlets.

15. The surgical instrument of claim 14 where the source of fluid comprises a water vapor source positioned within said wall for providing a flow of water vapor through the plurality of flow outlets.

16. The surgical instrument of claim 15 wherein the heating element comprises at least first and second RF electrodes.

17. The surgical instrument of claim 11 wherein the plurality of flow outlets are configured to direct flows therethrough in converging paths.

18. The surgical instrument of claim 11 wherein the at least one passage proximate the flow outlets is configured to direct a flow toward said axis.

\* \* \* \* \*